(12) United States Patent
Buote et al.

(10) Patent No.: US 6,681,198 B2
(45) Date of Patent: Jan. 20, 2004

(54) UNIFIED DATA ACQUISITION SYSTEM

(75) Inventors: William Buote, Bellingham, MA (US); Kenneth N. Rapp, Upton, MA (US); Burleigh M. Hutchins, Milford, MA (US)

(73) Assignee: VelQuest Corporation, Hopkinton, MA (US)

( * ) Notice: Subject to any disclaimer, the term of this patent is extended or adjusted under 35 U.S.C. 154(b) by 0 days.

(21) Appl. No.: 09/931,623

(22) Filed: Aug. 16, 2001

(65) Prior Publication Data

US 2002/0077785 A1 Jun. 20, 2002

Related U.S. Application Data

(63) Continuation-in-part of application No. 09/686,571, filed on Oct. 10, 2000.

(51) Int. Cl.[7] ................................................. G06K 7/10
(52) U.S. Cl. ........................... 702/185; 702/19; 702/23; 702/30; 702/32; 702/182; 702/183
(58) Field of Search ............................... 702/19, 21–23, 702/27, 28, 30–32, 50, 75, 100, 108, 114, 119–123, 179, 182, 183, 187–188; 707/4, 200; 717/4

(56) References Cited

U.S. PATENT DOCUMENTS

| | | | | |
|---|---|---|---|---|
| 4,873,633 A | * | 10/1989 | Mezei et al. | 356/39 |
| 5,694,595 A | * | 12/1997 | Jacobs et al. | 707/9 |
| 5,835,384 A | * | 11/1998 | Lin | 702/84 |
| 5,918,191 A | * | 6/1999 | Patel | 702/84 |
| 6,092,056 A | * | 7/2000 | Tull et al. | 705/36 |
| 6,192,320 B1 | * | 2/2001 | Margrey et al. | 702/84 |
| 6,399,025 B1 | * | 2/2002 | Chow | 422/102 |
| 6,366,924 B1 | * | 4/2002 | Parce | 707/104.1 |
| 2002/0060247 A1 | * | 5/2002 | Krishnaswamy et al. | 235/472.01 |
| 2002/0107452 A1 | * | 8/2002 | Kwong | 600/509 |

\* cited by examiner

*Primary Examiner*—Marc S. Hoff
*Assistant Examiner*—Carol S. Tsai
(74) *Attorney, Agent, or Firm*—John E. Toupal; Harold G. Jarcho

(57) ABSTRACT

A system for securing and validating the management and reporting of laboratory data wherein the taking of data at remote data-taking stations is denied absent electronic verification of both equipment and individual qualification, and wherein access to the data is denied absent electronic verification of individual authority.

23 Claims, 22 Drawing Sheets

VelQuest UDA – PROCEDURE MANAGER

System Procedure  Help

PM001.01 — VelQuest

Registered Procedures — 115

Sub-Systems | (Category - All) ▷ | (Active Status - A) ▷ | Register | Update

| Category | Procedure Name | Procedure ID | Version | Revision | Status |
|---|---|---|---|---|---|
| Mikes Second T | UDA Test | 2 | | | Approval Pro |
| Mikes Second T | File Test | 3 | 1 | 1 | Process |
| Test For Rob | UDA Current | 4 | 1 | 1 | Current |
| Test For Rob | Test for Rob Current | 6 | 1 | 1 | Current |
| Mikes First Test | UDA Test | 7 | 1 | 1 | Draft |
| Mikes First Test | UDA Test | 8 | 1 | 2 | Draft |
| Mikes First Test | UDA Test | 9 | 1 | 1 | Draft |
| Mikes First Test | UDA Test | 10 | 1 | 1 | Draft |
| Mikes First Test | UDA Test | 11 | 1 | 1 | Draft |
| Mikes First Test | UDA Test | 12 | 1 | 1 | Draft |
| Mikes First Test | UDA Test, No Revision | 13 | 1 | | Draft |
| Mikes First Test | UDA to IUDA | 14 | 1 | 1 | Draft |
| Mikes First Test | UDA to UDA | 15 | 1 | 1 | Draft |
| Mikes First Test | UDA to UDA | 16 | 1 | 1 | Draft |
| Mikes First Test | UDA to UDA | 17 | 1 | 1 | Draft |
| Mikes First Test | uda to uad | 18 | 0 | 1 | Draft |
| Bills A Procedure | Personnel Monitoring | 403.031 | 1 | 9 | Current |
| Mikes First Test | UDA to UDA | 19 | 1 | 1 | Current |
| Mikes First Test | UDA to UDA | 20 | 1 | 1 | Draft |
| Mikes First Test | UDA to UDA | 21 | 1 | 1 | Draft |
| Mikes First Test | File to UDA | 23 | 1 | 1 | Draft |
| Mikes Second T | UDA to UDA | 24 | 1 | 1 | Draft |
| Mikes Second T | File to File | 29 | 1 | 1 | Draft |
| Mikes Second T | File from UDA | 30 | 1 | 1 | Draft |
| Mikes Second T | File from UDA | 32 | 1 | 1 | Draft |
| UDA Test | UDA from File | 40 | 1 | 1 | Draft |
| UDA Test | File from File | 41 | 1 | 1 | Draft |

Security Manager
Instrument Manager
Report Manager
Procedure Devel.

User: Bill Buote  /TS: 2                5/16/00 6:00:33 PM

FIG. 5

VelQuest UDA – PROCEDURE EXECUTION

System Procedure Filter Help

◁ Back     PE001.01

Procedure Sessions — 117

Sub-Systems | Users

Security Manager

Instrument Manager

Report Manager

Procedure Manager

| Procedure Name | Status | Proc. ID | Ver. | New Rev. | Resume Lot # | Version | Status | Las |
|---|---|---|---|---|---|---|---|---|
| Test Procedure 2 | | 1775 | 1 | | 9087897 | Rob Alan | In Process | 5/1 |
| Test Procedure 2 | | 1775 | 1 | | 54654 | Rob Alan | In Process | 5/1 |
| Test Procedure 2 | | 1775 | 1 | | 3124 | Rob Alan | In Process | 5/1 |
| Test Procedure 2 | | 1775 | 1 | | 987987.3 | Rob Alan | In Process | 5/1 |
| Test Procedure 2 | | 1775 | 1 | | 86456 | Rob Alan | In Process | 5/1 |
| Test Procedure 2 | | 1775 | 1 | | 7556 | Rob Alan | In Process | 5/1 |
| Test Procedure 2 | | 1775 | 1 | | 88675669 | Rob Alan | In Process | 5/1 |
| Test Procedure 2 | | 1775 | 1 | | 6787676 | Rob Alan | In Process | 5/1 |
| Test Procedure 2 | | 1775 | 1 | | 796756 | Rob Alan | In Process | 5/1 |
| Test Procedure 2 | | 1775 | 1 | | 9879867 | Rob Alan | In Process | 5/1 |
| Test Procedure 2 | | 1775 | 1 | | 123456 | Rob Alan | In Process | 5/1 |
| Test Procedure 2 | | 1775 | 1 | | 8067 | Rob Alan | In Process | 5/1 |
| Test Procedure 2 | | 1775 | 1 | | 556754 | Rob Alan | In Process | 5/1 |
| Test Procedure 2 | | 1775 | 1 | | 678567456 | Rob Alan | In Process | 5/1 |
| Test Procedure 2 | | 1775 | 1 | | 978987.4 | Rob Alan | In Process | 5/1 |
| Test Procedure 2 | | 1775 | 1 | | 676767676767 | Rob Alan | In Process | 5/1 |
| Test Procedure 2 | | 1775 | 1 | | 13245 | Rob Alan | In Process | 5/1 |
| Test Procedure 2 | | 1775 | 1 | | 796857 | Rob Alan | In Process | 5/1 |
| Test Procedure 2 | | 1775 | 1 | | 55336788 | Rob Alan | In Process | 5/1 |
| Test Procedure 2 | | 1775 | 1 | | 432654 | Rob Alan | In Process | 5/1 |
| Test Procedure 2 | | 1775 | 1 | | 36346 | Rob Alan | In Process | 5/1 |
| Test Procedure 2 | | 1775 | 1 | | 97868976 | Rob Alan | In Process | 5/1 |
| Test Procedure 2 | | 1775 | 1 | | 78956434 | Rob Alan | In Process | 5/1 |
| Test Procedure 2 | | 1775 | 1 | | 4536 | Rob Alan | In Process | 5/1 |
| Test Procedure 2 | | 1775 | 1 | | 55334 | Rob Alan | In Process | 5/1 |
| Test Procedure 2 | | 1775 | 1 | | 3636363 | Rob Alan | In Process | 5/1 |
| Test Procedure 2 | | 1775 | 1 | | 4432 | Rob Alan | In Process | 5/1 |

— 179 New Resume

User: Bill Buote /TS: 2     5/16/00 6:05:27 PM

| VelQuest ePMC – PROCEDURE EXECUTION | | | | | | | _ □ × |
|---|---|---|---|---|---|---|---|
| Procedure  Help | | | | | | | |
| ◁ Back | | | | | | | PE002.01 |
| Sub-Systems | Current Procedures —187 ▽ Start Find All Versions —195 | | | | | | VelQuest |
| | Category —183 | Procedure Name | Procedure ID | Ver. | Rev. | Version | |
| | Test for Rob | UDA Current | 4 | 1 | 1 | Current | ←193 |
| Security Manager | Test for Rob | Test for Rob Current | 6 | 1 | 1 | Current | |
| | Mikes First Test | uda T0 uad | 18 | 1 | 1 | Current | |
| | Mikes Third Test | Validation Testing | 600 | 4 | | Current | |
| | Test for Rob | Astra SOP, On the VQServer01 | 2001.01 | 01 | A | Current | |
| | Test for Rob | Astra SOP on VQServer01 | 2002.02 | 01 | b | Current | |
| | Test for Rob | New Drake RTF Document | 1620 | 1 | 1 | Current | |
| | Mikes Fourth Test | File Server | 345.325.5634 | 23 | | Current | |
| | Bills A Procedure | Bills Lost Test | 12345678590123456 | 01 | 01 | Current | |
| Instrument Manager | Another Test | Test Number 01 | Barr015789 | 01 | 01 | Current | |
| | Test for Rob | Test Procedure 2 | 1775 | 1 | 1 | Current | |
| | Bills Demo | CREAMC0094873 | BMS0094873 | 01 | 14 | Current | |
| | Another Test | testing | wer309– | | | Current | |
| | Security Testing | security test | 6052 | | | Current | |
| | Bills Demo | Test of a new document created just now | Bill002 | 1 | 1 | Current | |
| Report Manager | Bills Demo | JP | IP002 | 1 | 1 | Current | |
| | Bills demo | Personnel Monitoring | 401.9587 | 1 | 1 | Current | |
| | UDA Test | JP Instrument Test | JP-PE | 1 | 1 | Current | |
| | Viewer Testing | File Server example | 8003 | 1 | 1 | Current | |
| | Test for Rob | USP 23 Method (Modified) for Caffeine Po | USP 23 | 1 | 1 | Current | |
| Procedure Manager | Bills Demo | Caffeine Potency by HPLC | 0000–1234 | 1 | 1 | Current | |
| | Add Method | documentuma | 1007 | 1 | 1 | Current | |
| | Add Method | UDA Boseda | 1008 | 1 | 1 | Current | |
| | Add Method | UDA from servera | 1009 | 1 | 1 | Current | |
| | UDA Test | PE4_2 | PE42 | 1 | A | Current | |
| | Document Testing | Examples for Procedure Conversion Guide | 1243 | 1 | 1 | Current | |
| | Security Testing | PE4_3 | PE43 | 1 | 1 | Current | |
| | Bills Demo | Status Test | BB Status Test | 1 | 1 | Current | |

181—

User: Bill Buote /TS: 5000    09/28/2000 12:13:55 PM

Data Review

Procedure Name: IP  
Procedure ID: IP002  Ver: 1  Rev: 1  Sample ID: BB045

| AT | OL | OD | SD | An | UDA | Field Label | Field Value | Who | How | Lot # | EIN |
|---|---|---|---|---|---|---|---|---|---|---|---|
| | | | | | 1 | Cold Reading | 75.2 | Bill Buote | EC | | |
| | | | | | 2 | Cold Reading C | 35.97778 | Bill Buote | FM | 654 | |
| | | | | | 3 | [Test Field] (1) | | | | | |
| | | | | | 3 | [Test Field] (2) | | | | | |
| | | | | | 3 | [Test Field] (3) | | | | | |
| | | | | | 3 | Shift | 4 | | | | |
| | | | | | 4 | Std Conc | 5.897 | Bill Buote | MN | | |
| | | | | | 6 | 50 g Reading | + 5.568 | Bill Buote | DB | BB200 | |
| | | | | | 6 | 200 g Reading | | Bill Buote | EC | 12344 | |
| | | | | | 6 | 250 g Reading | | | | | |
| | | | | | 7 | Weight Reading (1) | | | | | |
| | | | | | 7 | Weight Reading (2) | | | | | |
| | | | | | 7 | Weight Reading (3) | | | | | |
| | | | | | 8 | Cold Reading 1 | | | | | |
| | | | | | 8 | Warm Reading | | | | | |
| | | | | | 8 | Cold Reading 2 | | | | | |
| | | | | | 9 | Temp Reading (1) | | | | | |
| | | | | | 9 | Temp Reading (2) | | | | | |
| | | | | | 9 | Temp Reading (3) | | | | | |
| | | | | | 11 | First Reading | 8.61 | Bill Buote | FC | M001 | |
| | | | | | 11 | Second Reading | | | | | |
| | | | | | 11 | Third Reading | | | | | |

| SD | Who | Date/Time | Field Value | Reason | How | Sample ID | EIN |
|---|---|---|---|---|---|---|---|
| | Bill Buote | 09/14/2000 1:13:13 PM | 18 | Initial Value | MN | | |
| | Bill Buote | 09/14/2000 1:32:49 PM | 21 | Heater was slow | MN | | |

Procedure Name: Simple Procedure 1
Procedure ID: SP01   Version: 1   Revision: 1
Field Label: Reaction Temp   Field Index: 1   Sample ID: BB877

Audit Trail

Begin New Procedure Session(s)

Procedure Name: Testing 4001
Procedure ID: 4001　　Version: 1　　Revision: 1

Enter Sample ID(s)

Sample ID

[Add ▷]
[Edit/Replace]
[Remove ◁]

Assigned Sample IDs

Assign Security Attributes Values

Location: Wilmington
Lab: QA
Project: Pharma

[Accept]　　[Cancel]

FIG. 13

| VelQuest UDA - INSTRUMENT MANAGER | | | | | | □ ☒ |
|---|---|---|---|---|---|---|
| Instrument Help | | | | | | |
| ◁ Back | | | | | | IM001.01 — 121 |
| Sub-Systems | Registered Instruments | | | 343 ↗ | 345 ↗ | VelQuest |
| | (Labs All) ▽ | (Instruments All) ▽ | (Status All) ▽ | Register | Update | Inactivate |
| | Location | Lab | Instrument | Manufacturer | Model Number | Status | EIN |
| | Westborough | QA | BALANCE_1 | Sartorious | BH12 | Active | EIN Balance #1 |
| | Westborough | QA | THERMOMETER_ | SensorSoft | ST6154C | Active | EIN Electronic Ther |
| | Westborough | QA | PARTICLE_SIZE | Malvern | Particle Size Ana | Active | EIN Particle Sizer |
| | Westborough | QA | Virtual Instrume | Virtual Instrume | VT-01 | Inactive | EIN |
| | Westborough | QA | dfgf | Virtual Instrume | VT-01 | Inactive | gdf |
| | Westborough | QA | Clock | VelQuest | VQClock (v1.0) | Active | EIN Clock |
| | Westborough | Stability | GC | SensorSoft | ST6154C | Inactive | EIN120 |
| | Wilmington | QA | GC | | | Active | EIN2 |
| | Westborough | QA | GC | General Electric | QE-200 | Active | EIN 200 |

Security Manager
Report Manager
Procedure Manager
Procedure Devel.

▽

User: Bill Buote  /TS:  2                                               5/16/00  5:54:50 PM

VelQuest UDA – INSTRUMENT MANAGER
Register   Help

IM002.01
VelQuest

General Information – Sartorious B112

General   Connection   Test

General

Instrument Data Source                           Version
VQ_INSTRUMENT_LIBRARY ▷                          0.5

Manufacturer                      Model Number
Sartorious                        B112

Serial Number                     VQ Version
SN A123c-456                      1.0

Instrument Type                   Instrument EIN
Balance_3                         EIN Balance #1

Location                          Lab
Westborough ▷                     QA ▷

Connection Type                   Status
VQ-IB ▷                           ☒ Active Description ─ 347

User: Bill Buote  /TS: 2                         5/16/00  5:55:36 PM

FIG. 22

| VelQuest UDA – SECURITY MANAGER | | | | | _ ☐ ✕ |
|---|---|---|---|---|---|
| System User Edit Help | | | | | SM001.01 |
| ◁ Back | | | | | VelQuest |
| Sub-Systems | Registered Users | | | | |
| | [Department – All] ▷ [Status – All] ▷ | | Register Update Inactivate | | |
| | Full Name | Department | Status | Description | |
| Instrument Manager | Rob Alon | Development | Active | | |
| | Damien Steiger | Development | Active | | |
| | Mikew Condon | | | | |
| Report Manager | Wayne Domeier | Development | Active | | |
| | Bill Buote | CTO | Active | | |
| | Janine Steiger | SQA | Active | | |
| | Joe Perrault | SQA | Active | | |
| Procedure Manager | Bull Shannon | QA | Inactive | | |
| | John Doe | Analusis | Active | | |
| | Claude Hatfield | Development | Active | | |
| | David Mancini | Development | Active | | |
| Procedure Devel. | Fred Astaire | Development | Inactive | | |
| | Buck Rogers | QA | Active | | |
| | Tom Jefferson | Development | Active | | |
| | David Hasselhoff | Development | Active | | |
| | Fred Penner | Development | Active | | |
| | Barbara Walters | Development | Inactive | | |
| | Jean Harlow | Actress | Active | | |
| | Fred McNeil | Development | Inactive | | |
| | Kevin Lettko | Customer Support | Active | | |
| User: Bill Buote /TS: 2 | | | | | 5/16/00 5:42:17 PM |

| VelQuest ePMC – REPORT MANAGER | | | | □ □ ⊠ |
|---|---|---|---|---|
| System Report Filter Help | | | | |
| ◁Back | | Report Tables Updated on 9/5/00 at 14:22 By Mike Condon | | RM001.01 VelQuest |
| Sub-Systems | Registered Reports [(Category – All) ▽] [(Status – All) ▽] Register Update Run Report | | | |

| | Category | Report Name | Report ID | Version | Status |
|---|---|---|---|---|---|
| | VelQuest Support | Load Error Report | V0001-ER01 | | Current |
| Security Manager | VelQuest Support | Bills Test | B001 | 1 | Draft |
| | VelQuest Support | report | vq003 | 357 | Draft |
| Instrument Manager | Test of Sever | test 01 | test 01 359 | | Approval P |
| | Damien's Category | Damien Report 1 | 1 | 1 | Draft |
| Report Manager | | | | | |
| Procedure Manager | | | | | |

User: Bill Buote /TS: 5038      09/28/00 5:01:33 PM

UNIFIED DATA ACQUISITION SYSTEM

This is a CIP of U.S. Pat. application Ser. No. 09/686,571 filed Oct. 10, 2000, entitled Process-Linked Data Management System.

FIELD OF THE INVENTION

The present invention relates to systems and methods for obtaining, modifying and certifying data. More specifically, it relates to systems for securing and validating the inputting, manipulating, accessing and certifying of laboratory data and information such as test, measurements, test results, and test reports, especially during the development, pre-market evaluation and production of chemical and pharmaceutical products.

BACKGROUND OF THE INVENTION

During the development and production of many pharmaceutical and chemical products it is necessary to perform various tests and evaluations and maintain various records, then to manipulate the results of these tests and evaluations and prepare various reports that interpret and summarize those results. Such activities are generally performed in accordance with a set of laws and guidelines provided by the agency, such as the FDA, which controls or approves the market-release of the products and Standard Operating Procedures (SOP's), prepared by the manufacturer's internal Quality Assurance department (QA), or by an independently contracted auditor.

It is estimated that in the pharmaceutical laboratory 70% or more laboratory staff time is spent on documentation related to these tests, not actual laboratory operations. Cycle times from sample arrival to certificate of analysis are often quoted at 10 to 15 days. The QC/QA review cycle often challenges the data or the analysis, generating investigations to support the conclusions. Out of spec or out of trend results discovered during review are well beyond the time of the operation that generated them. To reduce cycle time in the laboratory, it is imperative to present error free, valid measurements.

Several computer-based data management systems specifically intended for use in such analytical laboratories have been designed over the years and are known generically as Laboratory Information Management Systems (LIMS). LIMS systems and chromatography data systems are common systems in pharmaceutical labs. While these systems often archive the analytical results, and provide reports, they are usually oriented too late in the process to insure original data integrity.

The inventors believe that a critical need exists to capture, validate and secure laboratory data as close to the source as possible. Technology is needed which performs this function with simple equipment and clear interfaces for laboratory personnel and instruments.

Under presently intended procedures, authorized analysts are provided with SOP's and, using properly calibrated instrumentation, perform the aforementioned tests and manually record the aforementioned data in accordance therewith. Once all data has been collected, it is transcribed into a batch record within a computer for interpretation and manipulation, and thereafter, for compilation into such reports as might be dictated by the SOP. The agency, auditor, or QA inspector can view the report(s), while simultaneously viewing the SOP and the supporting data to interpret the report and judge both its validity and its acceptability.

The approval and certification agencies for pharmaceutical products and many chemical products, such as the FDA, generally require the performance of such tests and evaluations and the production of such reports in conjunction with both development and production. Performance of these tests, access to the resulting data, and ability to manipulate it must be strictly limited to only qualified and authorized individuals, and only properly calibrated and specified equipment may be used. These requirements result in a tremendous physical and logistical problem, as the evaluation periods can be lengthy and huge quantities of data often accrue. Since present methods fail to recognize many anomalies in these requirements until the report-writing phase, that being the final phase in the process, tremendous delays and expense result when such anomalies prove results erroneous or invalid, polluting the batch record and causing the need for extensive re-testing so late in the process.

LIMS systems of some sort have always been essential tools in such research and development labs, in-process testing labs, and quality assurance labs as are involved in such testing and reporting. Typically, a LIMS is a software program loaded into the computer that receives the data collected from the instruments, either electronically or manually, manipulates and interprets it, maintains it, and presents it for independent inclusion in the required report(s). This information can thus be sorted and organized within the batch record or externally into various report formats based upon the type of report required.

As recently as the nineteen-seventies, laboratory notebooks and handwritten notes were the preferred tools used to track and record information. Thereafter, although handwritten notebooks are still in use today for certain data, custom-designed LIMS were configured by individual laboratories to allow certain analytical instruments to communicate directly with the main server. Such "in-house" systems, which are still being used to this day by many labs, can take considerable time and cost to develop, can require considerable resources and attention to maintain, yet still require many manual steps and documentation stages in order to satisfy most approval and certification requirements.

Even with the use of a LIMS, once data has been collected, it must first be downloaded, either manually or electronically, into the LIMS' batch record file. Each such recordation thus created presents an additional need for preservation and additional point of possible transcription error. Additionally, the recording of such data, which is generally proprietary, in and from numerous locations, increases the potential for access to this data by unauthorized individuals and presents a serious security concern.

Generally, data is either recorded manually or stored within a data collection system associated with the collecting instrumentation itself. For example, if an electronic scale is used, the weight data collected will normally be stored in a memory within that scale. Although this data can be transferred electronically to the server to minimize error, the need to maintain and report details about that original record is not eliminated.

Since the introduction of customized LIMS, great strides have been made in the electronic interfacing of instrumentation and data manipulating equipment. These have made feasible and provided an incentive for the development of a truly universal system to connect all instrumentation with both the server and the SOP's to thereby integrate all data, procedures, and results into one cohesive batch record which can produce one cohesive and inclusive report. This further provides an opportunity to reduce the record-keeping burden by minimizing record maintenance requirements, to improve security, and to expedite the evaluation process. Further, the cumbersome need to manually compare and interpret test results against the SOP can be eliminated and the discovery of invalidities and discrepancies prior to the final stage of the process can be realized.

By linking the testing, recordation and manipulation of resulting data, the generation of reports directly with the process itself, and by doing so while maintaining electronic control over access to this data to those who are so qualified and authorized, as provided by the present invention, it becomes possible to greatly streamline and expedite the approval process and ensure data validity.

OBJECTS OF THE INVENTION

It is an object of the present invention to provide a laboratory data management system in which access to data and authorization to manage that data are linked directly with the computer and instrumentation to provide resulting data whose validity is ensured.

It is an object of the present invention to provide a laboratory data management system in which data access is more rigidly secured.

It is an object of the present invention to provide a laboratory data management system in which data manipulation is more rigidly secured.

It is a further object of the present invention to provide such a system in which unauthorized access to or manipulation of data is impossible.

It is a further object to provide a system in which security is improved through the elimination of many written records and in which the unauthorized access to data records can be significantly reduced.

It is a further object to provide a system that is more universally adaptable to a variety of laboratory environments.

It is still a further object to provide a data management system that verifies that procedures are being properly followed on a real-time basis by authorized and qualified individuals to ensure that improprieties are recognized immediately.

It is still a further object to provide a data management system that verifies that operators are qualified to perform tests and access information on a real-time basis.

It is a further object to provide a data management system that verifies that equipment is properly calibrated on a real-time basis to ensure that variations are recognized immediately.

Further objects and advantages of the present invention will be best appreciated and more fully understood in reference to the herein-described preferred embodiment and the appended drawings.

SUMMARY OF THE INVENTION

The present invention is a universally adaptable Process-Linked Data system (PLD) for managing and reporting laboratory data wherein the procedures of the SOP itself are used to manage the performance of tests, to receive and record the resulting data, and to generate the required reports.

A unified data acquisition system is provided to simplify the laboratory environment. Since collecting data in conformance with the latest federal regulations (21CFR Part 11) requires that the data sources be identified, that the data be put into a secure repository and that access be restricted to authorized personnel, the present PLD Record Storage system will provide a compliant repository for electronic records in the laboratory.

The PLD Procedure Execution and Management system provides for primary data capture as an integral part of executing standard test procedures in the laboratory. Only authorized personnel may perform transactions that add, change, or affect data in any way. Means of identifying the persons performing the transactions is required.

Grouped identifiers are not allowed by FDA regulations. Since conventions for user ID's and passwords vary from one company to another, a customer SOP must be prepared to specify user name and password practices. The present PLD system has settings to allow enforcement of the uniqueness, frequency of change and re-use requirements specified in the SOP. When biometric identification of individuals is used, the system can also ensure that unique individuals are identified.

Terminal "sessions" must be established during which an identified individual is making data entries or controlling the collection of data from instruments. The terminal device may not be left unattended while the session is active. If the operator leaves the terminal device, she/he must close the session to prevent unauthorized entries. It is common to have an automated data collection activity that was started during a valid session continue after the session is closed. Another need is to enable a different individual (either to take over in case the original person is no longer available, or to act with higher authority) to initiate a terminal session and interact with ongoing data collection. The new individual must be properly identified and all data tagged with his identity.

The access control records of PLD are themselves stored in the PLD data base. The system allows for biometric identification of people and creates terminal sessions. Operators are able to log out. A reminder is displayed to attend the terminal at all times until log out. Terminal sessions may be resumed by any authorized person. All data collected is tagged with the operators identity.

The PLD Access Control System includes an enumeration of individuals together with the list of authorized activities and the list of authorized values for various security attributes. The access control system compares the security attributes of both the record and the individual to find a match before access to the record is granted. The system will only accept transactions from authorized individuals. Eligibility is based on user training on specific procedures. Access to training records is needed to determine eligibility. Enforcement by the system is an installation configuration switch. Supervisor approval is needed for non-eligible personnel to perform procedures.

21CFR Part 11 does not mandate electronic signatures, but without them associated paper documents must be produced, linked and signed. The present system supports a fully "paperless" system. An electronic signatures is an integral part of the present system.

An audit trail for each data field is maintained containing the entire data history. All changes are identified with the information including who performed the change (by entering the password or signature) and when was the change performed. A record of the data before the change was performed is kept. The reason for changes to the data are recorded.

Audit trail records must never be changed. They must contain unquestionable ties to the live data. No "rollback" facilities are available. The audit trail will grow over time and must be supported by hardware and software that introduces minimal delays in transaction processing.

There are three identification components: the operator, the equipment and the sample. This system will positively identify each of these.

Once the SOP is loaded into the PLD, a Method Instruction set (MI) is created which defines the test parameters and materials needed, prepares instructions for the instrumentation and test personnel, opens a batch record file, sets up a report outline, and follows the performance of each activity through to either a failure or successful conclusion. The system is equipped to either prompt the personnel to input each and every piece of information needed or obtain that data directly, and the system is equipped to either halt the process or alert the user whenever a specification is not met, an invalid test parameter is encountered, or erroneous or missing data is sensed, to avoid the possibility of having such discrepancies go unrecognized until later in the process or to propagate into other areas of the system.

This system even accepts data from Electronic Clipboard devices for manual input where an observation is made by lab personnel or where there is no means other than transcription to capture instrument readings.

The clipboard may be coupled to a vision device that can read barcode and alphanumeric displays, converting these displays into text. The clipboard device will also support infra red and wireless LAN communication to the data server.

A Secure Shell for PC based legacy instruments inserts itself at the application/operating system interface. It behaves mostly like a device driver for disk storage and/or printer devices. To the application it provides the entire Application Programming Interface (API) currently used by the application. Additional functionality is provided by dialog and data storage that is external to the legacy application. The dialogs acquire all additional information needed, maintain audit history, and prevent record corruption.

Data may be taken electronically from an instrument when the sample is processed. In this case the data is transmitted directly to the secure repository. Data may also be acquired from instruments operated by networked computers. The resulting analysis record filed on the networked computer is accessed and extracted data is transmitted directly to the secure repository. The detailed report of analysis is recorded in the repository also to support the extracted data. The Electronic Clipboard is used as the user terminal for control of the data transfer.

The instrument interfacing can be performed by personnel who understand the communication interface description of the instrument. An interface generator is used to generate interface descriptions that will be run in the server. Conventional programming is not required. A process for installing interface instructions into the system is available. The repository is physically and logically secured. The readings and associated ID's are immutable. The identity of the operator is verified when a terminal session is begun. The operator training records and the equipment calibration records are accessed before measurements are taken to alert the operator. A specific override is required by the operator to continue. The storage of the data includes means to capture or construct the state of operator training and equipment certification at the time of measurement.

An optional means for storing the expected value or range of values for measurements is provided. When expected values are specified, the data entering storage is compared to the expected values. An alert is provided to the operator when the measurement differs from expected values.

Devices for sample, operator and equipment ID capture are easy to use and require minimal change to present laboratory procedures. The data entry devices are primarily menu and select list oriented. Pen based and touch screen techniques are preferred.

In order to collect primary data at the source, either a wired connection or a local data terminal is available. This system will have a personal terminal. The personal terminal is easy to carry and to enter data on, can be set on the lab bench and used there or in the hands, has an operation time of at least 4 hours before routine service (such as battery charging or changing) must be performed. The terminals are recharged when not in use. In normal use, no cords are connected to the terminal. An optional use will connect the terminal to the network by a data cable. The system has either no connecting wires, or quickly plugable wires to small connection ports with high life connectors. The system displays the same dialogues from the system that are displayed on conventional PC devices. The system is able to provide positive identification of the device used. The system is able to scan bar codes for identification of samples, reagents, instruments, etc. Ethernet and TCP/IP are the preferred communication among devices connected by wires. IrDA standards are applied to devices that may communicate by infrared beams.

Once the data is obtained at remote data taking stations such as the aforementioned analytical instrumentation, it is transferred instantaneously to the main server for recording only in the batch record file, without being recorded at the remote data taking stations, to eliminate the need for record maintenance and auditing at those remote devices. Users are identified, and their authorizations and certifications are evaluated immediately. The functions that they can perform and the records that they can access are controlled by the PLD system. Equipment specifications and calibrations are confirmed immediately, and both raw and manipulated data are and need only be recorded in and reported from the batch record file. The resulting report integrates the test results directly with the procedure to provide a singular document which can be read and understood without the need to maintain and refer to other documentation such as notebooks, calibration records, user qualification certificates, instrumentation records and computer files.

Structured Query Language (SQL) standards are used for data access and a SQL database product is used under the present system.

Since each reading, observation or other report is called for by a specific prompt from the pre-approved procedures, and it is collected and stored in a tightly coupled fashion to that part of the procedure record for each sample, record maintenance is greatly reduced while security is greatly increased. The processing needed to interpret and move the data out of the instrumentation and into the batch record is done at the time the data is collected, not later when the report is prepared.

The distinct advantage of this approach will be apparent when information is being reviewed for compliance or other reasons later. Since the data is stored with the procedure and can be readily displayed, the original systems do not need to be consulted or preserved. The main advantage of this system becomes apparent when we consider the security and authentication requirements of the federal laws. By moving the data to a common procedure storage system, preferably without invoking any storage in the data collection system, all the record keeping requirements can be fulfilled in one system rather than many.

In the past, access control or security features of computer systems identified individuals and enumerated the functions that those persons were allowed to perform. Some examples of these functions might be; edit, operate, create procedures, administrate, etc. The data that results from these operations are usually stored in a file system or database, and complete security is obtained by only allowing the designated programs to operate on the data.

The present invention provides a system where individuals are identified and the record categories that they can manipulate are enumerated. A record storage system enforces the required authority for an individual to manipulate records, regardless of the processing system being used. This means that any record being retrieved is tested against the read authority of the individual. Likewise updates and creation of new records require that authority in the individual.

Finally, the audit trail required by federal law is built into the data storage system instead of the data processing system, as is the case in prior art systems. Since records must be stored for the duration of a defined record retention period, all activities performed on these records must also be recorded. Many different processing systems may come into being over this long duration, and it may be desirable to use not-as-yet-developed tools and equipment. There is a great advantage to having the audit trail generated and maintained by the storage system, without the need for special processing in every program.

Further advantages of the present invention will be best appreciated and more fully understood in reference to the herein described preferred embodiment and the appended drawings. of which the following is a brief description.

BRIEF DESCRIPTION OF THE DRAWINGS

FIG. 5 is a reproduction of the Registered Procedure display screen of the preferred embodiment, FIG. 6 is a reproduction of the Procedure Sessions screen of the preferred embodiment, FIG. 7 is a reproduction of the Approved Procedures screen of the preferred embodiment, FIG. 10 is a reproduction of the Data Review screen of the preferred embodiment, FIG. 11 is a reproduction of the Network Instrument Data Entry screen of the preferred embodiment, FIG. 12 is a reproduction of the Audit Trail Pop-Up screen of the preferred embodiment, FIG. 13 is a reproduction of the New Procedure Session screen of the preferred embodiment, FIG. 16 is a reproduction of the List of Registered Instruments screen of the preferred embodiment, FIG. 17 is a reproduction of the Device Registration screen of the preferred embodiment, FIG. 22 is a reproduction of the Login Dialogue screen of the preferred embodiment, FIG. 23 is a reproduction of the Registered Users screen of the preferred embodiment, and FIG. 24 is a reproduction of a Report Listing of the preferred embodiment.

DEFINITIONS

Figure 1:
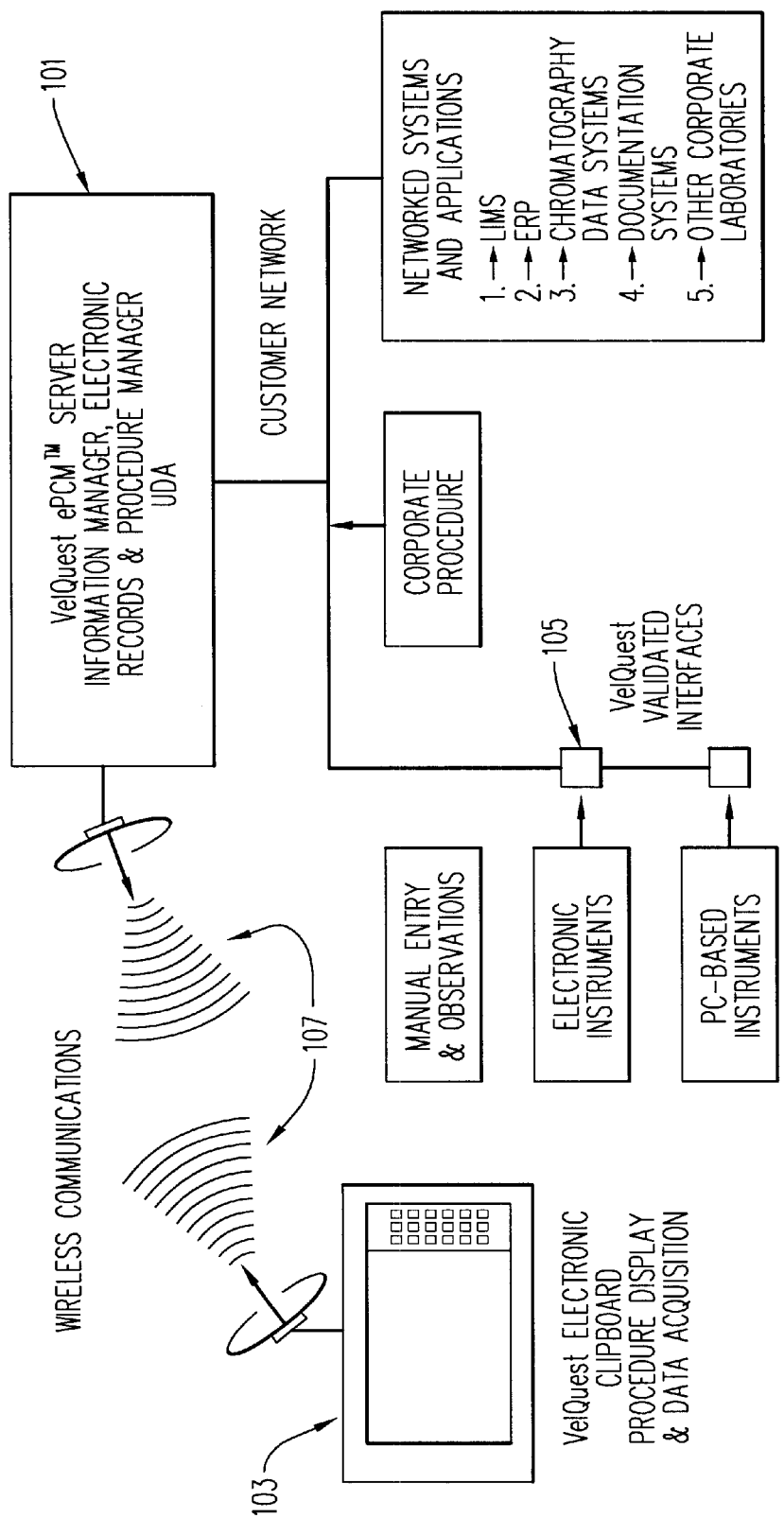
FIG. 1 is a schematic block diagram depicting the hardware of the preferred system and interfacing therebetween.

In order to best understand the following description, reference to these definitions should be made;

Application Server: A computer system which can access programs and records contained in the records management system, execute those programs and update records in the records management system.

Authentication: The process of checking the privileges of the identified individual who is causing records to be created or updated. This process uses an authentication data base that contains individuals names and unique privilege identification means that are compared to the security attributes of the records being created or updated. Authentication may never be over ridden or ignored.

Control Sheet: A simple report usually associated with a standard test method, or series of methods. The paper control sheet is filled out by the analyst(s) during performing the procedure(s). It contains all the final data required for product release or stability testing.

Electronic Clipboard: A device that is convenient to carry around in the lab. This device will display the output of the procedure interpreter and serve as a data collection and control device.

Eligibility: The process of determining the ability of an individual to create and modify records. The eligibility may be due to position, training, experience, delegation, or other reasons. It is most commonly a function of training. Eligibility may be over ridden or ignored in some situations.

Forwarding: Automatic actions based on PLD language specifications in a procedure that create a transaction file for another software system to read as input.

Identification: The process of determining the identity of the person using the system. This is accomplished by a combination of identifying string or token and password or biometric property.

Instrument Interface Device: A device that can connect to a laboratory instrument and to the bench-top network. The instrument interface will perform all control and protocol conversions required for acquisition of data from the instrument. No records may be stored in this device.

Parsing Specification: A description of an instrument data transaction used by the parsing function to extract a subset of information from the complete data stream. It includes descriptions of the triggers needed to cause the instrument output.

Procedure Interpreter: A software module that reads the procedure, identifies instructions intended for the data acquisition system, and carries out those instructions. The procedure interpreter is stored in the records management system and executes on the application server.

Procedure Session: A period of time relative to a standard procedure for specific items during which the procedure is applied to those items. There are usually three phases to the Procedure Session: the preparation and performance phase; the review phase; and the approval phase. The Procedure Session is available to only one authorized Terminal Session at a time.

Records Management System: A data base application which stores collected records and enforces record management disciplines on those records including all the requirements of 21CFR Part 11. These record management disciplines include the collection of meta-data identifying the sources and individuals responsible for the records, as well as a complete audit trail of all changes to the records.

Smart Shell: A computer program driver that mimics a disk device in the Windows operating system. Legacy applications may use this device as if it were a traditional disk drive. The driver will recognize data patterns as new storage or updates to existing storage. It will generate a dialogue in the Windows system to collect any required meta-data to fulfill record storage requirements. The smart shell will cause all information to be stored in the record management system.

Terminal Session: A period of time, relative to a particular terminal device, during which a known individual is interacting with that terminal device. A policy that requires personal attendance by that individual to the device as long as the terminal session is active must be enforced. The individual must "log out" or otherwise end the terminal session prior to leaving the device unattended.

Transaction File: A sequential file on a networked computer that is output by a software system for use by a second different software system. The second system reads the file and in doing so completes a transfer of data from the first system to the second system.

PLD Language Specification: Delimited statements contained in test procedures that describe the format, source and destination of data. These statements are interpreted by the PLD language interpreter to perform data collection and record keeping operations.

DESCRIPTION OF THE PREFERRED EMBODIMENT OF THE INVENTION

Figure 2:
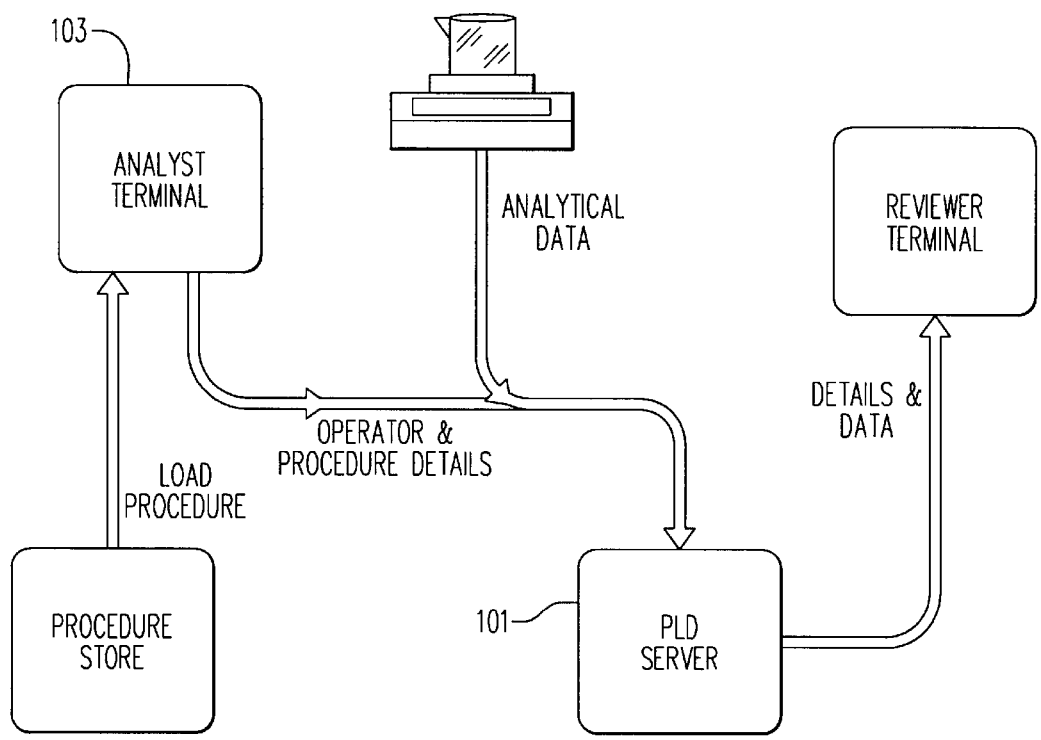
FIG. 2 is a flow chart depicting the flow of data in a system according to the preferred embodiment of the invention.
Figure 3:
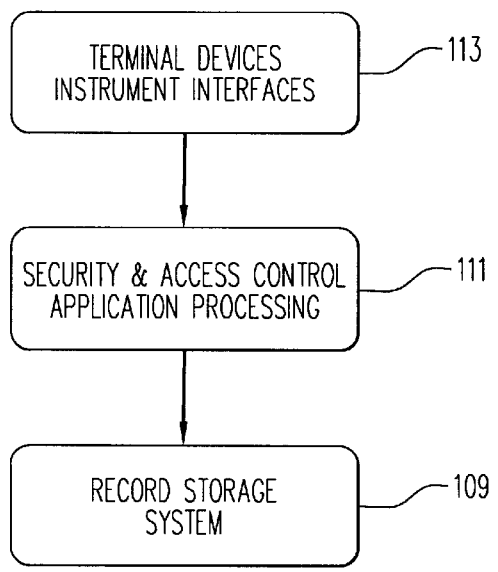
FIG. 3 is a schematic representation of the preferred system's three-tier architecture.

A Process-Linked Data Management System in accordance with the present invention is now described with reference to FIGS. 1 through 23 and the above definitions. As depicted in FIGS. 1 and 2, the system comprises the following hardware components:

Record Storage System (server) 101,
Electronic Clipboard 103,
Instrument Connection units 105, and
Radio Frequency LAN equipment 107.

The overall computer architecture is "Three-Tier Architecture" with very thin clients (incapable of storing records). The three tiers consist of: a data base server foundation layer 109 where all data is stored and secured; a process or "middleware" layer 111 where the application program logic is performed; and a client layer 113 where the user interface is presented. The data base server and the middleware services will normally run in the same processor system, but may be run on separate processor systems. The supported operating system for the data base server and the middleware server is Windows NT 4. Supported operating systems for client are Windows NT and Windows 98. The Record Storage System consists of an SQL compliant database engine housing the PLD data.

The middleware layer runs several functional applications:

The Procedure Manager 115,
The Procedure Execution Module 117,
The Procedure Development Module,
The Instrument Manager 121,
The Security Manager 123, and
The Report Manager.

The Electronic Clipboard is a display terminal or notebook computer for individual operator use and having the following features:

Pen-based, and
Wireless networked.

Since the person performing the laboratory analysis can carry the terminal, it has wireless connections to the network infrastructure. The client application may be run on clipboards, notebook computers or desktop workstations.

The Instrument Connection units are a family of small devices providing network connection to the server, instrument connection capability and operator panel connections. These units have the following features:

RS232 connections
Ethernet connection to network
Only translates protocol

The first Instrument Connection unit of the PLD system will support two RS232 ports only. The Instrument Connection unit also provides for physical attachment to the instrument to detect instrument changes. These devices may also have connections for infrared communication to the hand held terminals.

The Record storage system is a network-connected server with the following properties:

Is physically secure,
Is logically secure preventing unauthorized access to change data,
Is a high reliability system consisting of an enterprise grade electronic storage system and a remotely located parallel mirror of the primary system,
Ethernet network connection,
SQL standard data base access,
Assures record management meta-data is collected, and
Provides a partitioning feature of the database to support active archiving of historical data.

The connection to mobile clipboard devices in the lab uses IEEE 802.11 standard RF Ethernet networking. The frequency is in the 2.4 gHz band and is Direct Sequence Spread Spectrum (DSSS) mode of transmission. Units operating at 2 mbit/sec or greater are acceptable.

Figure 4:
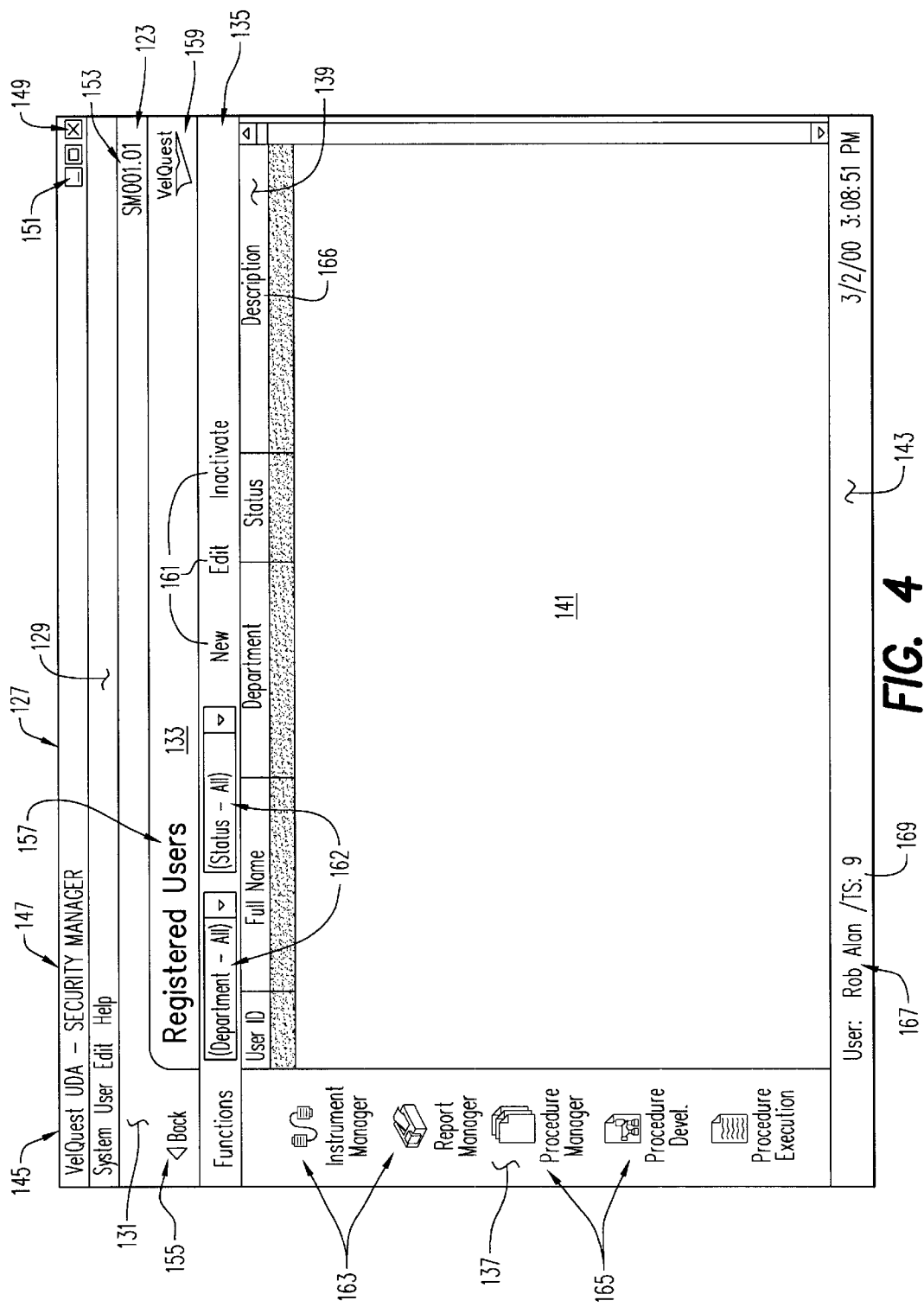
FIG. 4 is a reproduction of the basic User Interface screen of the preferred embodiment.

The basic user interface design is built on a consistent look for the major functional screens. FIG. 4 demonstrates this look.

Each screen shares the following common areas:

Title Bar 127,
Menu Bar 129,
Info Area 131,
Caption 133,
Button Bar 135,
Left Navigation Bar 137,
Column Headings 139,
Data Area 141, and
Status Bar 143.

All screens are at 600×800 resolution. The display mode for each window depends on the screen resolution set for the computer. If the screen resolution is set at 600×800, all windows will appear in maximized mode. If the display mode is set higher than 600×800 then all windows will appear in window mode. Window mode windows may be moved around on the desktop, but may not be resized.

The Title Bar is the typical Windows-type title bar, which carries the product name 145 and major function 147. It will also feature the upper right Windows-type buttons. The X button 149 will perform the same function as the "back:" selection on any screen. The Minimize button 151 will be available to place the application on the task bar. There is no Maximize button.

The Menu Bar line contains a standard Windows-type menu. In principal, all functions that may be performed in the screen can be accessed using the Menu Bar with a mouse. Additionally, all functions may be accessed using the keyboard arrow keys and accelerator keys are assigned to all functions.

The Info Area contains a unique string 153 identifying each screen and a back button 155.

The Caption displays a helpful description 157 of the data being displayed in the Data Area. It also features a logo 159 at the right edge, which will move when processing is taking place, but will remain steady when user input may be accepted.

The Button Bar features single click buttons 161 for the most frequently used functions associated with the data display. These buttons do not replace any functions available using the Menu Bar. Additionally, pull down boxes 162 may appear, which will allow single selections from frequently used key word lists, causing a subset of data to be displayed.

The Left Navigation Bar is a vertical area on the left side of the screen. This area will have icons 163 and captions 165 describing the major functional modules of the system. The currently selected module icon will be displayed in a contrasting style to the unselected modules. When a selection event occurs on an icon, the system will exit from the currently selected module and open the module indicated by the newly selected icon. Only modules that are available to the logged on user will be shown in the Left Navigation Bar. The Left Navigation Bar may not appear on screens used at deeper module functions.

The Column Headings 166 will appear whenever tabular data is displayed in the Data Area. These will indicate the nature of the data in each column. The headings will also be buttons which when pressed will cause the table to be sorted according to the data in the column. Successive button presses will alternately sort the table by ascending and descending order of the selected column.

The Data Area is where the information specific to the screen function is displayed. This may be a tabular display or any other format appropriate to the data. When the display is tabular, the ability to highlight a row and select an action using the highlighted row will generally be available. As this is a heavily used area of the PLD, large fonts and boxes are used.

The Status Bar contains at least the following information:

Logged on user name (the full name of the user who is currently logged on) 167,
Terminal Session ID (an identifying number for the current terminal session) 169,
Procedure Session ID (an identifying number for the current procedure session) 171, and
Date/Time Stamp 173 in the format mm/dd/ccyy hh:mm:ss am. (the time will be local time taken from the server. The setting of the date and time format is controlled by the operating system local specification).

After login, only functions that the user is authorized to perform will appear in the various menu bars and navigation bars of subsequent screens. Grayed out selections are used only to indicate selections that the user is authorized to do, but are not available in the current context of the application.

When a columnar form is displayed in the data area, the user is able to select an area of rows and columns and use standard Windows-type copy functions to place data on the Windows clipboard.

A calendar icon 175 is displayed on the right side of input boxes where dates are entered. Pressing the calendar icon presents a pop up calendar for date selection. The selected date is transferred to the data box when the calendar pop up is closed. The internal storage of a time stamp is a three-component record. The Windows data serial and time serial for local time at the server and the time zone offset are stored.

The background of all Data Entry Fields is white. When data is entered but not yet accepted into the system data storage, the field background is yellow. Only one data field may be changed at a time in a panel with multiple data boxes on it. When a data field is changed, the background of all other data fields is changed to gray and the field is locked. Gray background is also used to indicate a locked field when a panel is initially displayed.

The Procedure Manager provides the ability to view all procedures registered in the PLD. A registered procedure is one known to the PLD system by number, version and name. These are identical to the installation organization's designators for the procedure. The Procedure Manager has the ability to set up categories to aid in organizing procedures. These are specific to the PLD system only. To register a procedure, the location in the form of a Universal Resource Locator (URL) of the procedure must be supplied along with the status at the time of registration. The URL and the status may be updated, as needed using the Procedure Manager. All changes are recorded in the audit trail.

The registration information consists of the following items:

A key 177 consisting of the procedure number and version,
The procedure name,
The procedure category,
The procedure status,
The procedure URL, and
The registration audit trail.

Procedure storage may be in the database of the PLD or in a corporate procedure store. The protocol field of the URL will indicate the type of storage system. The access methods supported are Windows NT file server and Documentum. Supported file formats for procedures are portable document format (.pdf) and rich text format (.rtf). Some registered procedures may be stored in the PLD database while others are stored in a corporate system at any time. Import and Export functions are provided to transfer procedure files between the PLD and standard disk files.

The logged-on User ID is passed to the corporate procedure store when accessing approved procedures. Proper access controls are the responsibility of the corporate store that is expected to return either the test procedure or an error code.

Procedure status may be In Draft, Process, Current or Superceded. Access to procedures will be granted to individual users based on procedure status. If the location of a procedure changes as a result of a new status, the URL used to locate that procedure must be manually updated using the Procedure Manager screen.

The Procedure Manager links to the edit facility for procedures stored in the PLD. Users who are authorized to edit procedures will be presented with the link. The procedure will be fetched and passed to the edit facility listed in the system installation options. The editor is usually a standard word processor such as Microsoft Word. Upon a save operation from the editor, the modified procedure will be storable only in the PLD with a "Draft" status. Customer corporate SOP's for test procedure validation and approval will be followed to change the status of an edited procedure and cause it to be stored in the corporate system if required. These SOP's must include mechanisms for updating the procedure registration database in the PLD.

The registered procedure display screen, FIG. 5, shows the current document revision of the current version of the registered procedure. A "View" menu option provides access to all versions and revisions of procedures registered. The display may be filtered on any of the columns shown. Deleting a procedure registration record may be done when the procedure status is superceded and no procedure sessions reference the procedure.

The Procedure Execution module presents a list of procedure sessions stored in the PLD, FIG. 6. Only procedure sessions where the security attributes match those of the logged-on user will be displayed. The common filters of user and status are available in pull down lists on the Button Bar. Any procedure session that the user is authorized to access may be viewed by changing the filter settings. The user can modify the individual default filter setting. The initial default filter will show the logged-on users in process procedures.

There will be a large number of procedure sessions stored in the PLD. Therefore a rich filter function is provided to allow multiple selections from each column of the procedure session table. The procedure session ID is a two-part identifier. The first part is the unique combination of procedure number, version and revision, and sample identifier. The second part is a sequence number that indicates multiple runs of the same procedure on the same sample. An example of a procedure session ID is P0403.897 LOT5798:02. This is the second session of procedure P0403.897 for LOT5798 in the system. The procedure version and revision are displayed in individual columns. Procedure terminal status may be:

Open

Closed

Open sessions are sessions currently in use by laboratory personnel at a terminal. Closed sessions are not active on any terminal. A procedure session may be open on only one terminal at a time. Access by a second terminal is not allowed. If an open terminal session record is found, the identified terminal is queried by the system to verify that the terminal session is still active. The terminal session software automatically maintains the terminal status of the procedure session. A procedure session may be connected to only one terminal session at a time. A terminal session may be connected to several procedure sessions of the same procedure at one time. Procedure session status may be:

In Process

ReDo

Completed

Reviewed

Reviewed and Locked

Approved

In Process sessions are uncompleted sessions. All data and annotation items may be added or changed as needed to complete the session. When all required data has been collected, and all data values are within limits specified in the test procedure or have user-entered reason codes, the procedure status may be changed to completed. No data entries may be added or changed in Completed sessions, but a reviewer may add step annotation. The reviewer may change the status to Reviewed, Reviewed and Locked, or back to In Process if data needs to be corrected. No data entries may be added or changed in Reviewed sessions, but a reviewer may add step annotation. The reviewer may change the status to Approved, Reviewed and Locked, or back to In Process if data needs to be corrected. No data entries or annotation may be added or changed in Reviewed and Locked sessions. The reviewer may change the status to Approved. Authorized users may change status to ReDo. No data entries or annotation may be added or changed in Approved sessions. The status of the procedure session may not be changed, except that authorized users may change status to ReDo.

Figure 8:
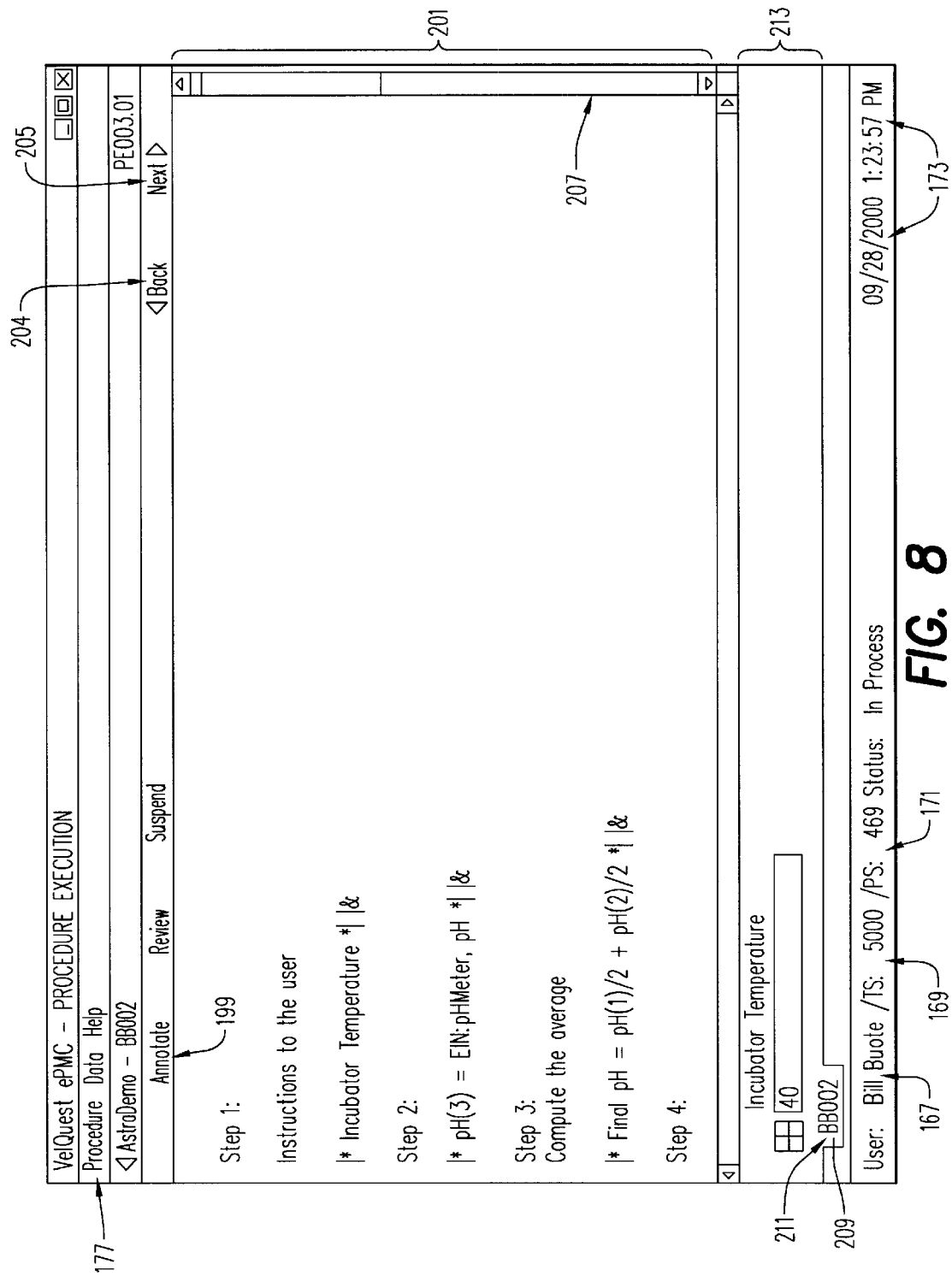
FIG. 8 is a reproduction of the PLD Data screen of the preferred embodiment.

Completed, Reviewed and Approved status change may be performed by authorized individuals using the "Procedure" menu 177 of FIG. 8. However, no person will be allowed to Review or Approve a procedure session where they initiated or completed the session. Electronic signatures are required when the status is changed to Completed, Reviewed and Locked, Approved and ReDo.

Selecting "New" 179 on FIG. 6 may start a new procedure session. The screen changes to a list of Approved Procedures registered in the PLD, FIG. 7. The required procedure may be highlighted using the Category column 181 and the column sort 183 features of the User Interface. Once the required procedure is selected, the new session is begun using the "Start" button 187. A dialogue box as depicted in FIG. 13 is displayed for entry of the Sample Identifier, or multiple sample identifiers for the new session(s). A rich filter function is available as the pop-up menu depicted in FIG. 14 for multiple selections in each displayed column. Normally, the current approved procedures 193 are displayed. If a prior version of a procedure needs to be used, the "All Versions" selection 195 will show prior versions of procedures.

The indicator 199 for step annotation may be pressed to display the annotation in a pop up window. This provides quick access to special comments recorded about the procedure session. Once a procedure session or a new procedure is selected, the procedure is retrieved using the URL in the Procedure Manager for that procedure number and version. The PLD language in the procedure is interpreted and used to display the data present in the PLD database, FIG. 8. The data display of the procedure is not in table form. The procedure execution display consists of three sections. The upper section 201 is the procedure text where each step, as delineated by the step mark in the PLD language, is displayed. The active step is indicated by colored marking. "Back" 204 and "Next" 205 buttons control the up and down movement of the highlighting to identify the active step.

A scroll bar 207 on the right side of the procedure display area allows movement by line or page through the procedure. Clicking anywhere on a step shown in the display area causes the current step to be set to that step.

When multiple procedure sessions have been started or opened, a selection bar 209 is displayed above the status bar. The selection bar shows all of the sample identifiers 211 of currently open sessions. Pressing one of the sample identifiers will cause that procedure session to be displayed.

In some steps, PLD specifications for data collection will appear. The procedure execution module uses these specifications to display appropriate data collection boxes 213 in the data collection area 214. Meta-data boxes 215 will be automatically generated in the middle section, the meta-data area 217. The meta-data boxes collect instrument identity and calibration information. The PLD registration information is accessed to determine what kind of data collection activity is appropriate for the instrument. The data collection boxes provide input fields 219 for user data entry, electronic capture display and file or database capture displays in the lower area. The middle and lower 221 sections are displayed as required by the data collection specifications in the procedure. The height of the lower area is dynamically adjusted to fit all data boxes in the step up to two lines of data boxes. When the area needed for data collection boxes exceeds two lines of data boxes, a vertical scroll bar will be displayed on the right side of the data collection box area. The meta-data middle area is displayed as required when an instrument is used in the step. Only one instrument can be used in a PLD step. When the active step has no data collection requirements, the entire data area is used to display the test procedure text.

Figures 9, 9A:
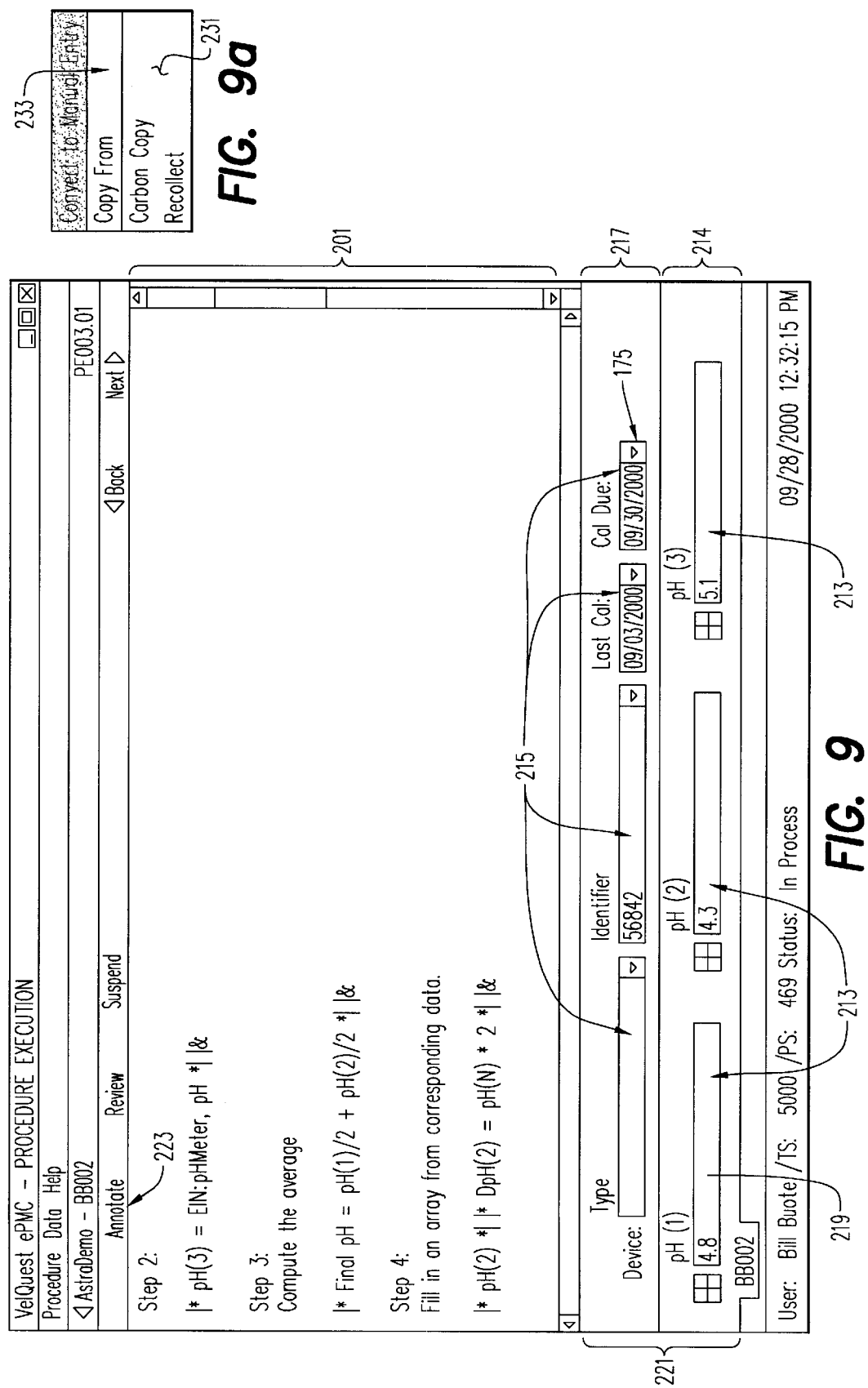
FIG. 9 is a reproduction of the Data Collection screen of the preferred embodiment.
FIG. 9A is a reproduction of Pop-Up Menu Selection screen of the preferred embodiment.

The screen of FIG. 9 includes a data collection area that allows the analyst to record the instrument readings manually or by capture from connected instruments. The meta-data area above the data area provides for entry of the required information. Recording the calibration date and due date is enabled by an installation option.

Figure 11:
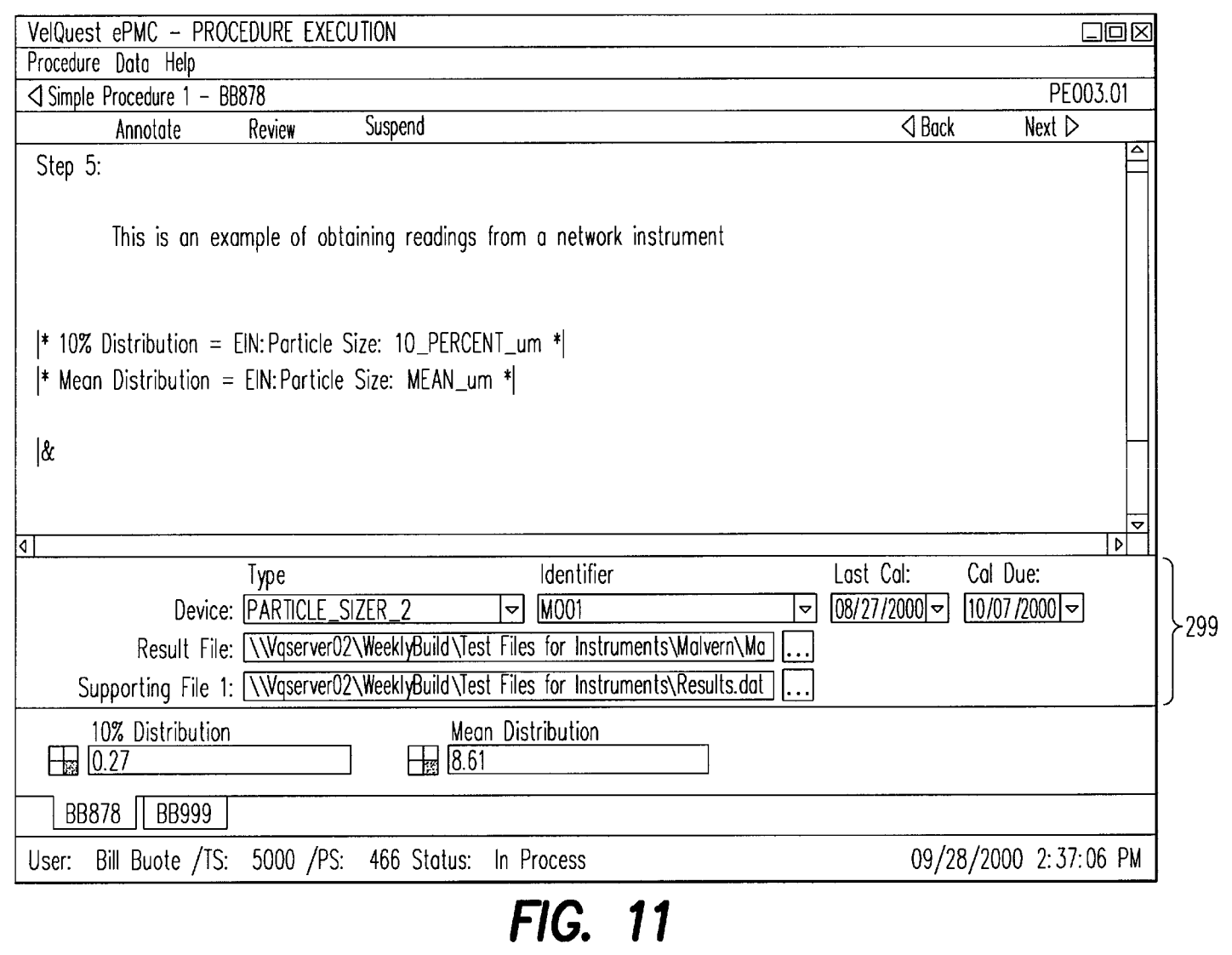

FIG. 11 shows a data collection area generated for a networked instrument. In addition to the file location, there is a need to collect information that represents the correct location of the file and a key to identify the location within the file where data will be extracted. When the instrument registration specifies capture of instrument method and/or raw data files, an additional URL box will be displayed for each specified file.

During execution of a procedure, annotation may be added to any step using the "Annotate" button 223 or menu selection of the screen shown in FIG. 9. A test box appears for entry of the annotation. The annotation may be changed at any time, invoking a standard PLD audit trail.

More than one procedure session may be open in the same terminal session as long as all open sessions are using the same procedure number and version. Data items which are common to all open procedures such as standard prep, reagents, mobile phase information, etc. may be entered into one procedure and transferred to all other open procedures by a pop-up menu selection (FIG. 9A). Copying data may only be done with values that are already recorded in the PLD database. Use of the copy selection 231 overrides the PLD input data specification in the procedure for the data in the other procedures. Another selection 233 provides an input override to copy information from another procedure session that is not open. This override can only read data from another procedure session that has the same procedure number and input field name.

A concise listing of all data collected is available from the data review function, FIG. 10. The display shows the name of the field and the latest value for each data item and displays blanks for any items not yet collected. The meta-data is displayed in columns after the data: Date, Time, Who, EIN, Reason Code and Capture Mode. The first column 235 contains an indicator 237 for data audit trail. Selecting the indicator causes an expansion or contraction of rows showing the complete data history. The second column 239 displays an out of limit indicator 241 for any data where the value exceeds the limits in the test procedure. The "OK" button 243 will return to the procedure execution display. The fourth column 245 displays an indicator 247 for supporting data. Supporting data may be either captured from an instrument or input from another procedure session. If the input data from another procedure session has a newer timestamp than the current session, the supporting data indicator will change to indicate so. Pressing the supporting data indicator will cause the supporting data to be displayed in a pop up window using a viewer appropriate to the data format.

Figures 14, 15, 15A:
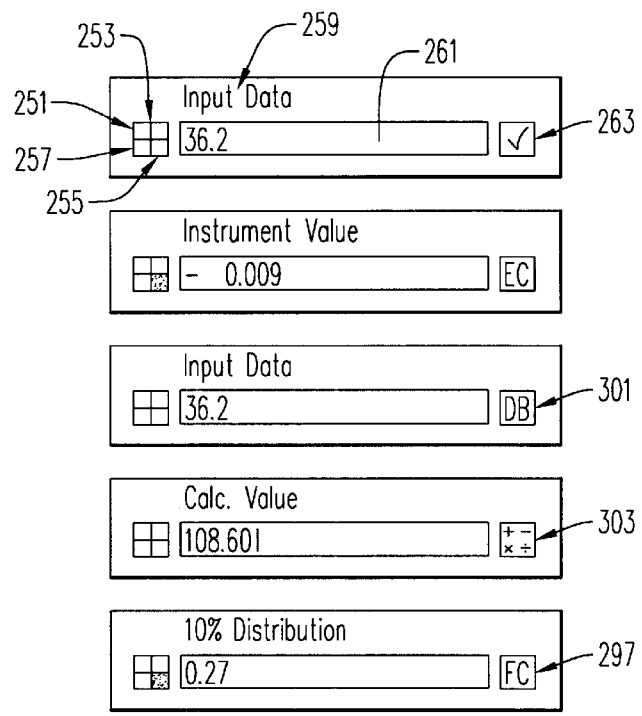
FIG. 14 is a reproduction of the Rich Filter screen of the preferred embodiment.
FIG. 15 is a reproduction of several data collection boxes of the preferred embodiment, FIG. 15A a reproduction of the Reason Code Dialogue Box of the preferred embodiment.

The standard data entry box, FIG. 15, consists of seven main elements (left to right):

The audit trail selector 251,

The out of limit indicator 253,

The supporting data selector 255,

The old data indicator 257,

The variable name label 259,

The data entry box 261, and

The action button 263.

The audit trail selector 251 appears whenever there is more than one entry and when the original entry has a user entered reason code. When pressed, the selector will cause the audit trail pop up window, FIG. 12, to appear showing the expanded detail audit trail of the individual data item. The column headings and actions are the same as those available in the data review function.

The out of limit indicator 253 will be displayed whenever the current value for the data box does not conform to limit specifications contained in the test procedure.

The supporting data selector 255 appears whenever the input data stream from an instrument has been recorded. Pressing the indicator will display a viewer for the input data stream. Recognized data streams such as graphic files, text files, etc. invoke standard viewers launched as an embedded process in the PLD. Non-standard data streams invoke a hex-ascii viewer. The supporting data indicator 255 on a data entry box is controlled by the latest entry in the audit trail. When viewing the audit trail, a supporting data indicator will appear for each entry in the audit trail as appropriate.

The old data indicator 257 will be displayed whenever any source data for calculated values is newer than the calculated value.

The data entry box 261 provides for entry of alphanumeric text. The variable name 259 from the procedure is displayed over the box. Some data boxes may have an associated format specification in the PLD specification. Manually entered values will be checked against the format specification when the action button 263 is pressed. If the entered value conflicts with the format specification a warning dialogue is displayed allowing the user to change the entered characters prior to recording the value in the PLD database.

The action button 263 optionally appears whenever the value in the entry box has not been committed to the PLD database, when an instrument capture action is available or a calculation can be done. These action buttons are used:

Commit data,

Capture data from a connected instrument,

Capture data from a networked instrument,

Transfer data from other PLD procedure sessions, and

Calculate data from other PLD data boxes.

The commit data button appears whenever an uncommitted value appears in the box and no other button could appear. Keyboard and pen entry is used to place the data value in the box. The user may edit the value to correct for typographical errors. When the value is correct, the commit data button is pressed, recording the value in the database. After recording the data the button is no longer displayed. The value may be changed at a later time by editing the value displayed in the box. When the value is changed, the commit data button is once again displayed. The modified value will be recorded when the button is pressed. The reason code dialogue will be displayed for all modified values.

The capture data from a connected instrument button appears when the meta-data ID selects a registered instrument that is connected to the PLD system. The button will indicate and trigger electronic capture of the data. The captured data is recorded in the database and displayed in the data box. The button is removed from the display when the data is recorded. The data may need to be re-captured for a variety of reasons. Initiating a recapture is done with a right mouse menu selection causing the electronic capture button to re-appear. The ability to manually change electronic data is controlled by an installation option. When manual changes are allowed, a keyboard or pen entry that changes the data in the box will cause the commit data button 263 to appear. In the case of any kind of change the audit trail, including reason code will be recorded.

The capture data from a networked instrument button 297 appears when the meta-data ID selects a registered instrument that is connected to the corporate network. This button functions like the connected instrument button, but uses the expanded meta-data bar 299 to identify the source data file.

Multiple data boxes parsed from a single data stream from an instrument may appear in a step. When this condition occurs, only the first of the related boxes will have an action button. The remaining related boxes have data captured at the same time as the first box.

The "transfer data from other PLD procedure sessions" button 301 appears when the data capture specification specifies a related PLD procedure sessions. This button functions like the connected instrument button, but uses the meta-data bar to identify the procedure session where the data is read. The initial procedure session displayed in the meta-data bar is the one where the sample ID matches the current procedures sample ID, if it exists. All procedure sessions for the related procedure are available in the selection list.

The calculation button 303 is displayed when a formula is specified in the PLD specification. Calculations may only use data from other data boxes in the same procedure session. If data is needed from sources outside the procedure session, a separate data capture box must be used in the procedure.

When data is changed, a standard dialogue 305 is displayed that requires entry of the reason for the change. The dialogue consists of a pull down list of previously established reason codes. The most recently used reason code is remembered for the terminal session and displayed as the default value the next time the reason code dialogue is shown. The logged-on user may be granted different levels of reason code authority: use predefined reason codes only; add special reason codes as needed; and add new reason codes to the list. If the user is limited to predefined reason codes, one of the displayed reason codes must be selected. If the user can enter special reason codes, the text is entered in the list box area. When the user is authorized to add new standard reason codes, the new code is entered in the list box area and a check box is displayed to make it a standard reason code. An installation option can be set that will require entry of the users electronic signature to record the reason code.

There may be a condition when an action is needed that is beyond the authority of the logged-on user. An alternate user may be added to the terminal session using a menu selection. While the alternate user is added, all security tests are based on the added user authority and all data recorded is identified with the alternate user's ID in the audit trail. The alternate user's electronic signature is required for any needed signatures. When the alternate user's authority is no longer needed, the alternate user must exit the session. The original user remains as the logged-on user with his or her authority.

The procedure interpreter reads the PLD specifications found in the test procedure and causes the data collection 214 and meta-data 217 areas to be displayed. The test procedure is displayed in the same format as it is viewed in its normal editor. Printed copies have essentially the same format also. Existing test procedures are converted to PLD test procedures by the addition of the PLD language for data collection. The original procedures may be in paper form or a variety of electronic forms. The converted procedures need to be stored in a data format acceptable to the PLD. In some cases, there may be reasons to continue to use paper test procedures. The PLD may still be used for primary data capture by creating a test procedure digest consisting of the PLD language for each step in the procedure where data is captured. The digest is stored in the PLD. Validation and linking of the digest to the approved procedure are handled by the customer's corporate SOP for test procedure approval.

The PLD language consists of readable keywords, tokens and variable names as illustrated by the following table, that do not interfere with the clarity of the test procedure instruction to the operator.

Step 1:
    This is an example of creating an input data box titled "Input data".
    |* Input Data *|
|&
Step 2:
    This is an example of reading a weight from a balance.
    |* Instrument Value = EIN:Balance: weight_g, F3.4 *|
|&
Step 3:
    This is an example of comparing an entry to a limit.
    |* Reaction Temp *|
    |* LIMIT: Reaction Temp > 20: "Temperature is too low." *|
|&

-continued

```
Step 4:
   This is an example of a calculation.
      |* Calc Value = Input Data * 3, F5.2 *|
|&
Step 5:
This is an example of obtaining readings from a network instrument.
|* 10% Distribution = EIN:Particle Size: 10_PERCENT_um *|
|* Mean Distribution = EIN:Particle Size: MEAN_um *|
|&
|* START REPORT *|
VelQuest Corporation
Initial Data:        |* Input Data          *|
Temperature:         |* Reaction Temp       *|
Small Size:          |* 10% Distribution    *|
Median Size:         |* Mean Distribution   *|
|* END REPORT *|
```

The PLD specifications are usually placed at the end of each procedural step that collects data. A step delimiter (|&) is placed at the end of each logical step in the test procedure. A special, delimited section (from "|*START REPORT*|" through "|*END REPORT*|") is placed at the end of each test procedure to provide a full data report for the data collected. This form is in a WYSIWYG format, with data box fill-in specified by the data field names taken from the body of the procedure.

The main statement types implemented in the PLD specification language are:

Selection specification,

Activation specification,

Data input specifications,

Data limit specification,

Data forwarding specifications, and

Data reporting specifications.

The selection specification provides a multiple choice or check box facility that provides classification of the type of sample or type of test being performed. Each multiple choice item has an integer value, Each check box item has a true or false value. Activation tags in other data specifications can test the value of a selection item.

The activation specification refers to a selection variable name and value. When the value in the specification matches the value in the selection variable, then the PLD commands for the current step are activated.

The data input specification will support data capture manually from the display terminal, directly from connected instruments, from data files on networked instruments and from data stored in other PLD procedure sessions. Transferring data from other PLD procedure sessions supports the consolidation of multiple analyses into a batch record that might be maintained in the PLD system. It also supports incorporation of data from instrument calibration, reagent prep, and standards prep procedures.

The data input specification consists of the following elements:

Data variable name,

Optional count

For Instrument Readings

Instrument keyword—EIN

Source EIN variable name

Reading name

For Input from Other Procedure Sessions

Procedure keyword—VDA

Input procedure number

Input variable name

For Calculated Results

=formula

Optional Format Specification

The count expression is either an integer that refers to a specific item of the array, or a whole array indicator followed by a count variable name or array size for operating on all elements of the array. The reading name must be the same as a field identifier set up for the instrument in the instrument parse library. The format specification includes controls on the type of entry, significant figures, decimal places, rounding and truncating. An installation option specifies the rules to be used for rounding the final result of calculations. The data limit specification tests the value in a data input box against one or more numerical limits. If the value is outside the limit a message specified in the limit specification is displayed for analysts' acknowledgement.

The data limit specification consists of the following elements:

a Limit: keyword, a Data variable name,

Limit expression, and

Alert message text.

The limit specification must appear in the same step with the data entry specification it applies to. The limit expression is tested with the data variable value. If a result is false, an alert 319 will be displayed using the alert message text. Two means of acknowledging the alert are available. One simply clears the alert and returns to the previous screen. In this case the system-generated indicator identifying initial data is applied to the value. The other means causes the reason code dialogue to be displayed as in FIG. 15A, allowing a user-entered reason code to be applied to the value. An installation option will enable acceptance of an out-of-limit entry by entering a reason code, Data forwarding specifications control the movement of selected data to other computer systems or to other procedure sessions stored in the PLD system. The data forwarding specification will be able to specify output formatting suitable to create a transaction file for other systems, such as LIMS and chromatography data systems. The data forwarding specification consists of the following elements:

Forward: keyword

Forwarding action specification

For Transaction Files

Destination URL of transaction file

List of data field names to be included

For Procedure Sessions in the Data Base

Procedure ID

Variable name where the data will be stored

The forwarding action specifies when the values should be forwarded. The possible values are:

In Process,

Completed,

Reviewed, and

Approved.

Forwarding while in-process causes the forward button to appear when the step is selected. Forwarding after completion, causes the Review or Approval to be activated when the procedure status is changed. The steps containing the forwarding specification will appear in the procedure display area 201. The person performing the review or approval must activate the forwarding function by pressing the forward button. A record of the forwarding action is stored in the standard PLD audit trail. Forwarding will cause a forward button to be displayed in the data box area for the step. The meta-data area will show the URL from the procedure and a key field. The final URL and the key field are entered by the analyst before pressing the forward button.

The standard technique to transfer data to another system from the PLD system is a transaction file. The file is generated according to the forwarding specification in the PLD commands. The destination URL is a network file specification selected at the time of data transfer. Specific forwarding interfaces for a variety of other systems may be made.

Data reporting specifications provide the WYSIWYG format for a formatted data report that is available at the end of each procedure. The data forwarding specification consists of the following elements:

The Report delimiter,

The WYSIWYG layout of the data report,

The data field references, and

The End delimiter.

The data report appears like a form in the procedure. Within the form, data field references cause the values of the data fields to be displayed when the report is viewed. Although not the only syntax useable for this purpose, the following is the BNF Definition of PLD Command Syntax of the preferred embodiment:

```
PLD_step => text | PLD_statement *[text | PLD_statement] bar&
PLD_statement => barstar data_statement | limit_statement
| select_statement | activate_statement | forward_statement
| report_statement |
report_variable starbar
data_statement => arrayname [= data_source ] [,formatspec ]
data_source => instrument | calc | PLDsource
instrument => EIN: source_ein : sourcefield
source_ein => name
sourcefield => name
calc => expression
PLDsource => PLD:procid:arrayname
formatspec => ftype length [dp length]
ftype => F|I|S
length => digit *[digit]
limit_statement => LIMIT: arrayname compexp: false_action
select_statement => SELECT: selectvar = set
activate_statement => ACTIVATE: selectvar = | < >
text_string | set
forward_statement => FORWARD: forward_action, forward_spec
forward_action => In Process | Completed | Reviewed |
Approved
forward_spec => transaction_forward_spec |
procedure_forward_spec
transaction_forward_spec => url_template: arrayname *[,
arrayname]
procedure_forward_spec => procid:arrayname = arrayname *[,
arrayname = arrayname]
selectvar => name
procid => textstring
report_statement => START REPORT | END REPORT
report_variable => arrayname | report_predefined
report_predefined -> PLD_Analyst | PLD_Sample ID | PLD_Date
| PLD_Reviewer | PLD_Approver
url_template =>
protocol://machine_name/[path_name/]file_name
protocol => file
machine_name => text
path_name => text
file_name => text
false_action => text_string
compexp => compop expression *[logicop compop expression] |
= set
expression => [unop] [(] [unop] arrayname | expression |
number [biop arrayname | expression | number ] [)]
set => = { text_string, text_string *[, text_string]}
arrayname => varname | varname (count )
count => digit *[digit] | varname
varname => name
number => [unop] digit *[digit] [dp digit]*[digit]
compop => =|>=|<=|<>|=<|=>|!=
logicop => and | or
unop => - | +
biop => + | - | star | / | ^
text_string => "text"
text => anychar *[space | anychar]
name => alpha*[alphanum]
alphanum => alpha | digit
anychar => %01% -> %7f%
alpha =>
A|B|C|D|E|F|G|H|I|J|K|L|M|N|O|P|Q|R|S|T|U|V|W|X|Y|Z|
a|b|c|d|e|f|g|h|i|j|k|l|m|n|o|p|q|r|s|t|u|v|w|x|y|z
digit => 0|1|2|3|4|5|6|7|8|9
dp => .
barstar => %7c%%2a%
starbar => %2a%%7c%
star => %2a%
bar => %7c%
```

Procedure Development provides a means to create or edit experiments and collect data. Each experiment is stored as procedure text in the PLD database under an experiment name and experiment number. Each time a new experiment is started both a new session and new experiment text will be generated. When the identifier for the experiment matches a previously entered identifier the next sequential experiment number is applied. The first screen is a list of experiment sessions, FIG. 6. Any in-process session may be resumed, or a new session may be started. When a new session is started, a choice is presented to start with empty text, or to start with the text of a previous experiment or a standard procedure. If a previous experiment is selected, a list of development experiments stored in the PLD database is presented for selection. The previous text is copied into the experiment text area and is prepared for data collection. Experiment text is stored like procedures, but in a separate area that is invisible to procedure manager and procedure execution. When a set of experiments leads to the preparation of a draft procedure, the draft procedure is handled by procedure manager and procedure execution.

When new experiment sessions are started, the experiment identifier and the experiment name are taken from the experiment text records. The test item identifier is entered in the same way a sample ID is entered in the Procedure Execution module. A free text field is also provided to enter a description of the experiment session;

During the course of running the experiment, all PLD commands operate and provide normal data collection facilities. In addition, the test of any step may be edited by pressing the "Edit" button when the highlight identifies the step. However, collecting data restricts editing to only those steps appearing after steps in which data has been collected.

A text-editing screen is displayed with the existing step text. The instructions to the analyst and the PLD commands may be edited. When the "Finish" button is pressed, the revised step text is displayed in the procedure execution window.

Alternatively, a data collection dialogue can be displayed showing appropriate meta-data fields and data collection boxes, allowing direct entry of the measured data and meta-data by the operator. When the data collection is completed, the appropriate PLD commands will be inserted into the experiment text by the dialogue process, so that the data collection activity may be automatically repeated at a future time.

Appropriate Meta-Data fields and Data Collection boxes will be displayed and data collection may be performed. While an experiment session is in process, the associated experiment text is stored in the PLD database in the same way as registered procedures. The experiment text is updated in the database at the completion of each edit operation. In this way the correct state of the procedure text is displayed when the experiment is displayed in a terminal session. When the experiment is changed to completed status, no further changes to the experiment text may be performed.

The Procedure Execution module is used when there is a need to repeat an experiment to collect more data without changing any of the experiment text. Experiment information is displayed in Procedure Execution as follows:

| | |
|---|---|
| Experiment ID | Procedure Number |
| Experiment Category | Procedure Name |
| Experiment Session | Procedure Session |
| Experiment Item | not shown |
| Experiment Description | not shown |

The Procedure Development module has a reporting mode that integrates the procedure text with the collected data. Each defined PLD step text is displayed, followed by the meta-data and collected data in a similar format to that shown on the screen. This report may be reviewed on the screen and printed.

The Instrument Manager provides the ability to register instruments in the PLD system. Any kind of instrument may be registered from simple indicating devices such as mercury thermometers to computer-controlled devices such as chromatographs. Some devices may have electronic connections to the PLD system. The entry screen of the instrument manager is the list of registered instruments, FIG. 16. The list of registered devices is presented with a simple sort facility on device type. Device type is an arbitrary grouping category entered at the time of device registration. New devices may be registered by pressing the "Register" button. Registration information is entered in the screen depicted in FIG. 17. Registered devices are initially registered as unconnected devices. The "Updates" button runs the instrument connection setup. The series of setup screens provides for input of the following parameters:

Type of connection,
Mode of data capture (Electronic, File),
Commands to device,
Data streams from device,
Creates data field keyword for PLD method language, and
Specifies recording the input data stream.

Figure 18:
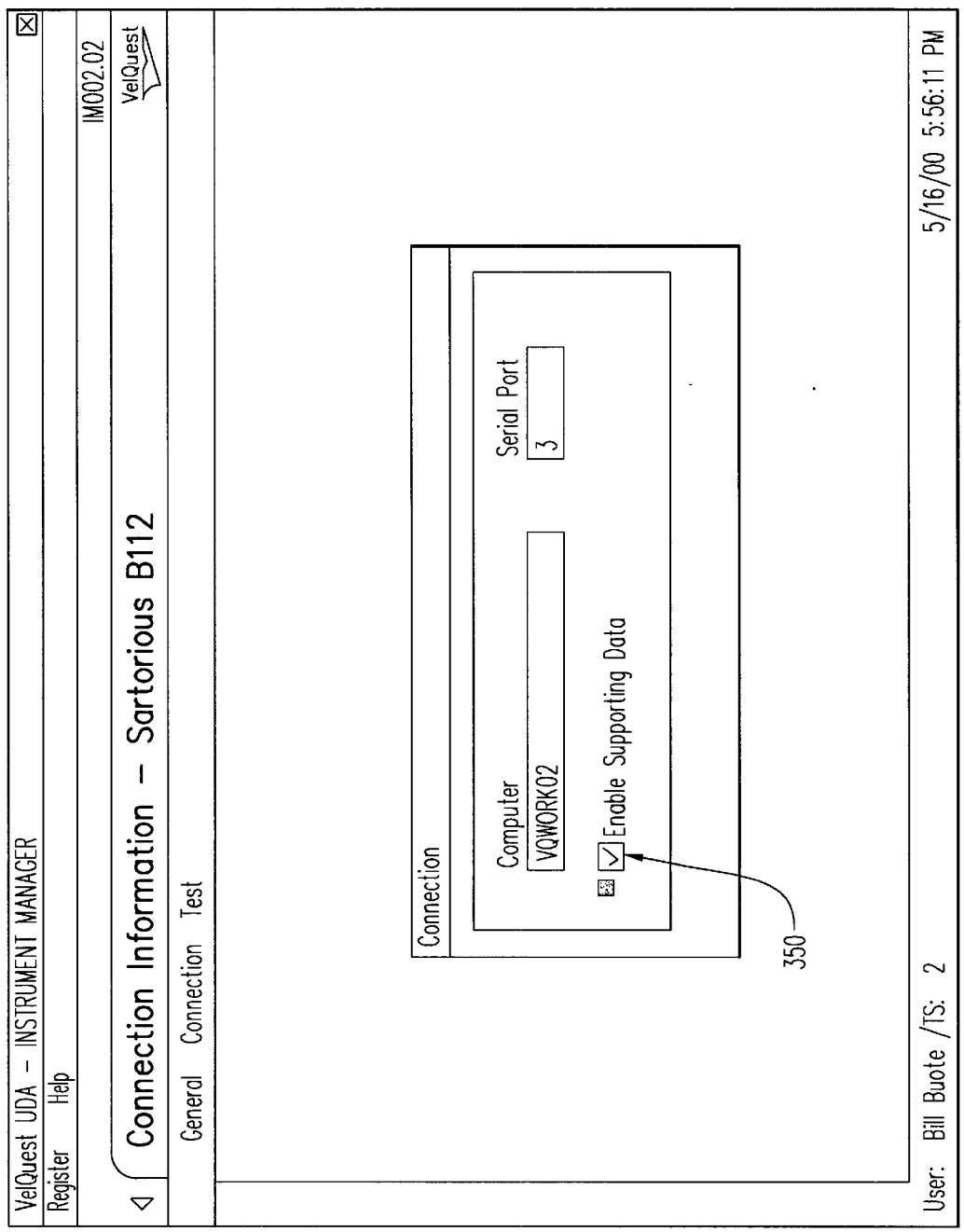
FIG. 18 is a reproduction of the Instrument Physical Output Connection screen of the preferred embodiment.
Figure 19:
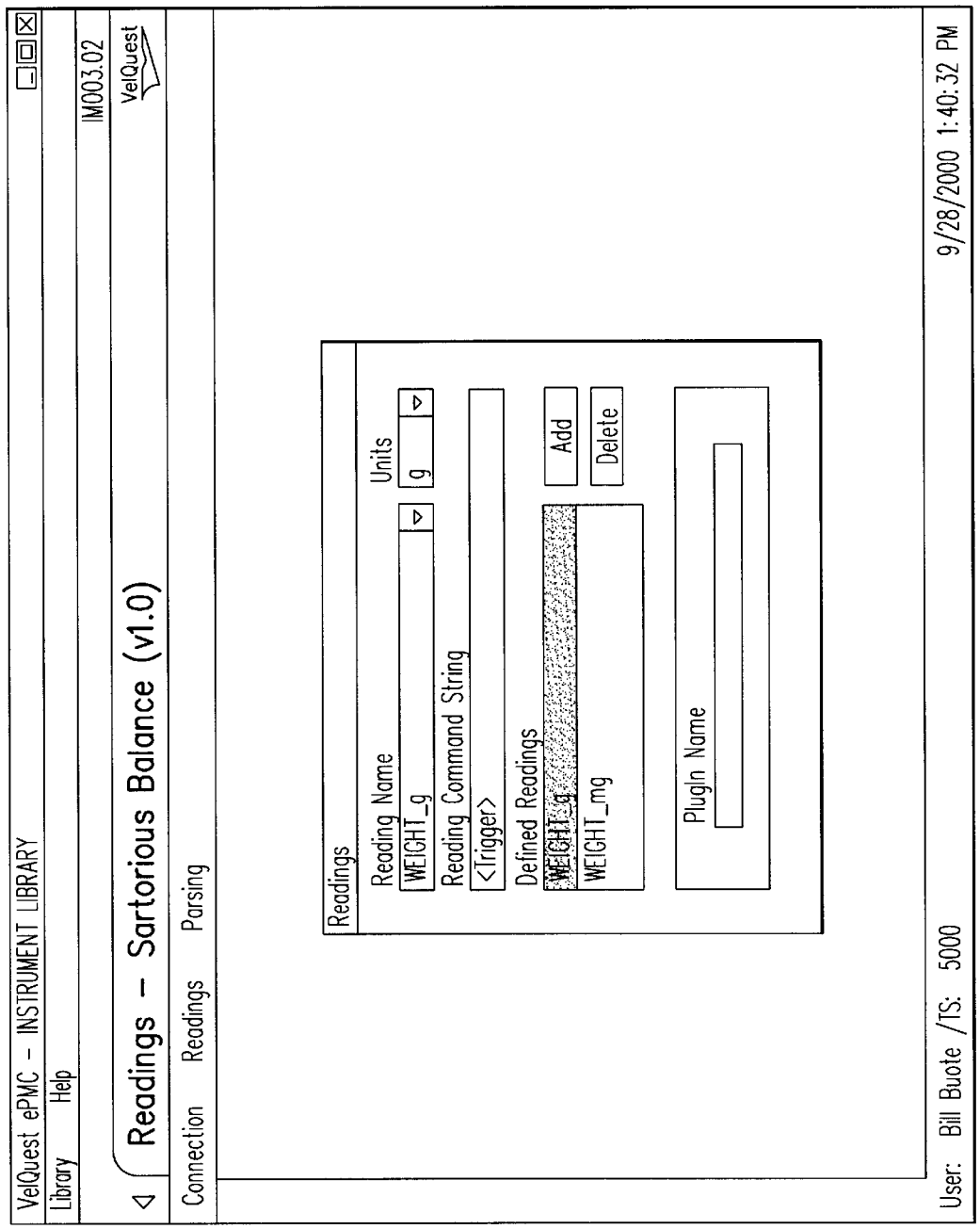
FIG. 19 is a reproduction of the Command Name screen of the preferred embodiment.
Figure 20:
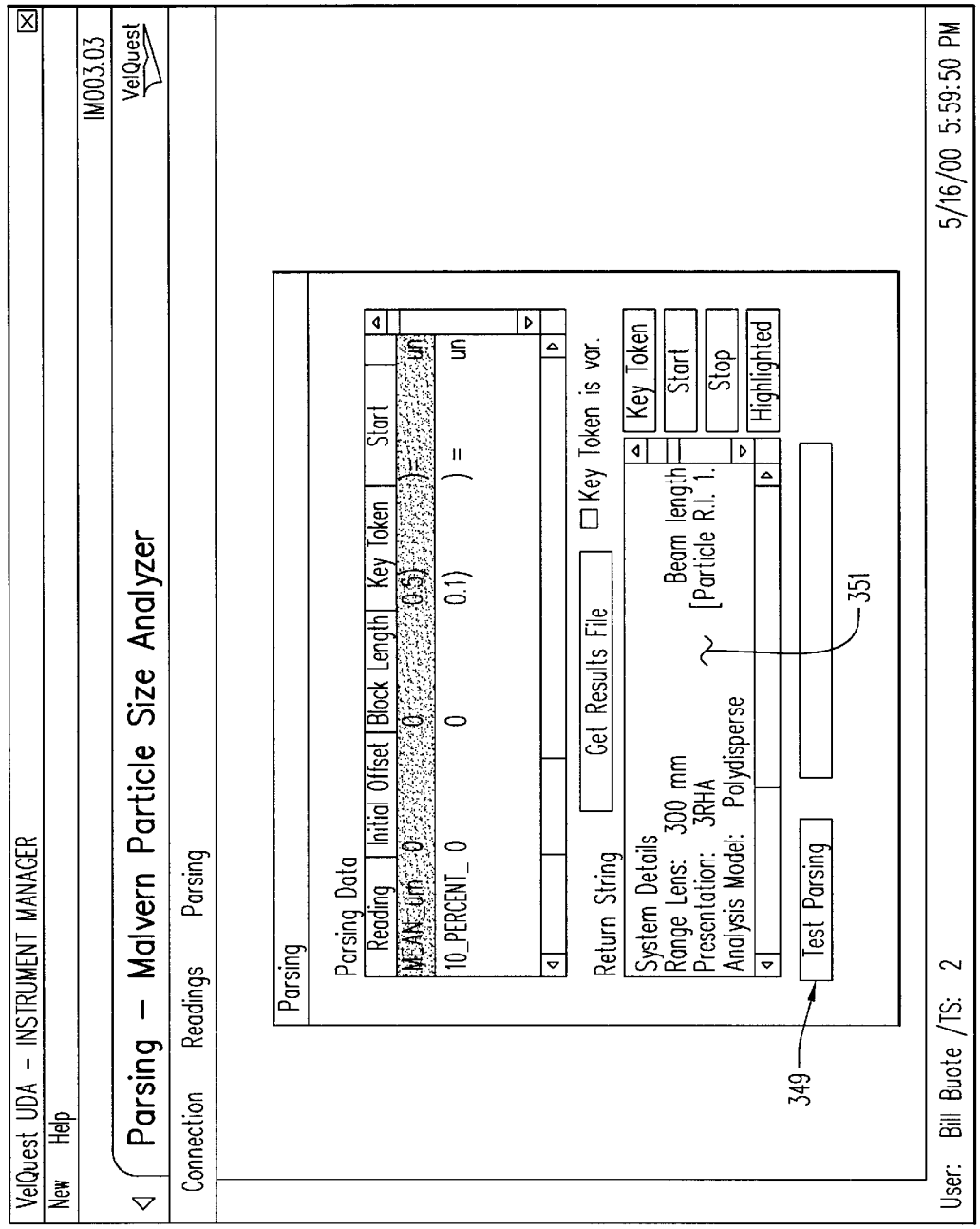
FIG. 20 is a reproduction of the Parsing Specification screen of the preferred embodiment.
Figure 21:
FIG. 21 is a reproduction of the Instrument Setup screen of the preferred embodiment.

The type of connection specifies the instrument's physical output connection, FIG. 18. The PLD Instrument Interface box (Ibox) is used for all connection types except a network connection. Depending on the connection type, an initialization string is defined by the instrument administrator to set parameters such as baud rate or data width. The PLD Ibox accepts these specifications and configures itself and the instrument as needed. The address or computer name and the port number of the instrument are also specified with the connection details.

There are two modes of data capture: triggered or collected through communications interface and network connections to the instrument. The usual network connection is to a computer running the instrument. In this case the input data stream is a file or data base query from the computer. In either case an input data stream may yield only one data value or multiple data values. Multiple data values are obtained from only one input data stream. The input data stream may be recorded in the PLD database.

Supporting data consisting of method files and instrument resident raw data files can be recorded in the PLD database together with the result files. Within the interface specification, each data collection activity is identified by a command name, FIG. 19. Each named command may have a trigger specification for the reading. If no trigger is required, the specification is left blank. A parsing specification to control extraction of data values from the input data stream must be supplied, FIG. 20.

To define parsing, an example return string must be available to the instrument administrator. The example may be obtained by pressing the "Test" button 349 that will acquire an actual data stream from the instrument and display it. Alternatively an example data stream may be typed into the display area 351. In both cases the data stream may be edited to enable a complete parsing specification. Once the example data stream is displayed, any number of individual data field specifications may be entered. Individual data field specifications consist of the following elements:

Format specifier,
Line and character count to start,
Start character string, and
Ending character string.

These specifications are largely entered graphically using highlighting on the example data stream to locate individual source areas.

Networked instruments usually have large data files covering a multitude of samples. For each command, the location of the data in the input data stream may depend on a key string or a positional count. The meta-data area of Procedure Execution provides input of key information to locate the correct area of the file for a given procedure session. The rules for finding the correct area of the file using the key are entered in the instrument setup, FIG. 21. These rules are based on matching the key string in the input stream, or counting blocks of data in the input stream. These parameters may also be imported from a library of previous instrument setups.

For each instrument, an option 350 is provided for controlling the recordation of the supporting data stream that is used to parse the resulting data values. The saved supporting data stream is stored in the PLD database together with the results.

The Security Manager consists of two major subsystems:
The User Authentication system and
The User and PLD Maintenance system The User Authentication system is invoked whenever a user attempts to gain access to the PLD system, and when user authentication is required for controlled events such as electronically signing a document or entering a reason code.

The User and PLD Maintenance system is used by the PLD System Administrator to authorize individuals for access to the system and to establish system installation parameters To gain access to the PLD system, a valid User ID and password is required. These are entered in a dialogue screen (FIG. 22) and validated against the appropriate user database. After successful identification the user's authorized activities and the user's security attribute lists are loaded into the system for reference by other modules. After successful login, a reminder is displayed warning the user not to leave the terminal unattended.

Optional biometric devices may be used to enhance user identification. The biometric devices are installed at all workstation computers where access to the PLD system is required. Personal terminal devices such as electronic clipboards and notebook computers do not have associated biometric devices. These devices use an infrared or other link to associate the personal terminal with one or more workstation computers equipped with both a biometric device and an IR or other port. After the IR or other link is established, the user may log into the personal terminal using the biometric device on the workstation.

Two modes of user identification are available. The first mode validates the User ID and password entries by the operating system. The PLD then grants access based on the PLD records for the User ID logged-onto the operating system. The second mode validates the User ID and password entries by comparing to records stored in the PLD database. The PLD then grants access based on the PLD records for the User ID logged-onto the PLD system.

Since the PLD programs are read from the server, a valid network login is required in either case to provide access to these programs. When the operating system is used for user identification, no further login screens will be displayed. When the PLD system is used for user identification, the PLD login screens will be displayed at the start of the PLD application. When the identification uses the PLD database, installation options specify the frequency of password change. The login screen has an option to change the password by entering the old password and a new password with double confirmation. If the time specified in the installation option has expired, the change password dialogue will be presented to the user with no other actions available except to change the password. The new password entered must meet installation options for length and uniqueness over the specified number of previous passwords.

The User and PLD Maintenance system provides the registration function for authorized users and provides for setting PLD installation parameters.

The identification of users by User ID and password is the fundamental identification mechanism. An installation parameter determines if the operating system (Windows NT) is the user database, or if the PLD user database will be used to identify the user. When a private user database is in effect, the user maintenance screens provide for entry of new User ID's and passwords. When the operating system user database is in effect, the user maintenance screens will provide access to the operating system list of users, allowing a subset of those users to be added to the PLD user database. Regardless of the identification data base used, supplemental information and two major categories of user authority information is stored in the PLD data base:

1. User ID
2. User department
3. User status
4. User Full Name
5. Authorization of activities
6. A plurality of security attribute lists The PLD administrator can add users, modify the descriptions and security attributes of users and inactivate users, using the menus. Over time some users will no longer be authorized to use the PLD system. However these users may be associated with recorded data. Therefore the User ID and Full Name and inactive status will be permanently maintained in the PLD database. The User ID may not be issued to any other individual. Inactive users may be reactivated at a later time. When only one PLD administrator is defined s/he may not be inactivated. The PLD administrator may not change his/her record.

Activities are defined as operations that may be performed using the PLD system. For example, editing a procedure, running a procedure and approving a procedure are activities in the Procedure Execution module. Each functional module of the PLD system specifies the activities that may be authorized. These activities will be presented as a list grouped by module. When additional modules are installed in the system, additional activities will appear under the new module heading in the security manager. The security manager has two activities that may be authorized: user maintenance and PLD option maintenance. During initial installation of the system an add user dialogue is displayed to cause an initial PLD administrator to be assigned. This dialogue will occur after the selection of the mode of user identification database occurs. A specific individual will be identified.

Security attributes are a set of fields attached to each data record. The exact number of fields may be varied to suit the application. These fields provide a set of descriptors for each record that are used to allow access to the record. Each user record has the ability to store a multitude of values for each of the security attributes. The names by which users will know each of the security attributes are setup as an installation option. These names are used for display only. Internal operations involving security attributes are identical for all attributes regardless of user assigned names. The number of security attributes actually used may be limited by an installation option. When limited, screens displaying the attributes will show the limited number. Records generated will have excess security attributes filled in with a "match all wildcard" value. When the number of security attributes is increased at a later time, old records will match any value in the user database. Users may have an unlimited list of specific values for each security attribute including wildcard values with sub-strings. For each value, an access level of either read or write will be assigned. Access to records is granted by matching all security attributes in the record with the list of security attributes for the logged-on user. The most limited access is granted.

The Registered Users screen, FIG. 23, is the entry screen for user maintenance. It provides access to each registered user as well as access to system wide installation options on the "System" menu pull down.

Each installation may tailor the operation of the PLD system to conform to its SOP's. The following options are available:

1. Location of User Identification data base
2. Supervisor approval for original data changes
3. Number of Security Attributes
4. Names of all Security Attributes
5. Password expiration interval
6. Required length of passwords
7. Number of previous passwords which must be unique
8. Allow manual entry of data from electronically connected instruments
9. Allow override of electronic data capture from instruments The Report Manager maintains a list of stored reports, together with the required information to run those reports. Each report listing, as represented in FIG. 24, contains these elements:

Report Name 355,
Report ID 359,
Report Version 357,

A report may be selected by normal selection methods. When selected to run, the report engine is started and the saved specification for the report are presented to the engine. If any tailoring of the parameters is needed, it is performed by the report engine software. New reports may be prepared using the report engine software. A dialogue 365 for the name of the report is presented. Upon saving the report, the Report Author, Date Created and Report Version are automatically entered.

Those skilled in the art will recognize that there are many variations of the invention that are within the scope of the invention, therefore, the invention is to be defined only by the limitations and the equivalents thereof which the following claims set forth.

What is claimed is:

1. A data managing and reporting system for laboratories engaged in the development or production of pharmaceutical or chemical products for human use and comprising:

one or more remote data-taking stations;

a central data managing and reporting device for receiving test data from said one or more stations and establishing pre-existing procedures for receiving said test data from said one or more stations; said procedures including test procedures required to obtain said data and requirements for the obtaining of said data by only certain qualified individuals; and means for transmitting said test procedures from said device to said one or more stations, transmitting said test data from said one or more stations to said device, requiring confirmation that an individual seeking to transmit said test data is qualified in accordance with said procedure requirements, and denying reception of said test data by said device absent said confirmation.

2. A data managing and reporting system according to claim 1 wherein each of said one or more stations is precluded from storing said test data.

3. A data managing and reporting system according to claim 1 wherein said means causes said one or more stations to request and receive said confirmation from said individual prior to transmitting said test data.

4. A data managing and reporting system according to claim 1 wherein said means causes said one or more stations to request and receive said confirmation from said individual prior to obtaining said test data.

5. A data managing and reporting system according to claim 4 wherein each of said one or more stations are precluded from storing said test data.

6. A data managing and reporting system for laboratories engaged in the development or production of pharmaceutical or chemical products for human use either internally or externally and comprising:

one or more remote data-taking stations;

a central data managing and reporting device for receiving test data from said stations and establishing pre-existing procedures for receiving said test data from said stations; said procedures including test procedures required to obtain said data and requirements for the obtaining of said data from only certain qualified stations; and means for transmitting said test procedures from said device to said one or more stations, transmitting said test data from said one or more stations to said device, requiring first confirmation that a station is qualified in accordance with said requirements, and denying reception of said test data by said device absent said first confirmation.

7. A data managing and reporting system according to claim 6 wherein each of said one or more stations is precluded from storing said test data.

8. A data managing and reporting system according to claim 6 wherein said means causes said device to receive said first confirmation from said one or more stations prior to accepting transmission of said test data.

9. A data managing and reporting system according to claim 8 wherein each of said one or more stations is precluded from storing said test data.

10. A data managing and reporting system according to claim 6 wherein said procedures include requirements for obtaining of said data by only certain qualified individuals, and said means requires second confirmation that an individual seeking to transmit said test data is qualified in accordance with said procedure requirements, and denies reception of said test data by said device absent said second confirmation.

11. A data managing and reporting system according to claim 10 wherein each of said one or more stations is precluded from storing said test data.

12. A data managing and report system for laboratories engaged in the development or production of pharmaceutical or chemical products for human use either internally or externally and comprising:

one or more remote data-taking stations;

a central data managing and reporting device for receiving and storing test data from said one or more stations and establishing pre-existing procedures for receiving and managing said test data, said procedures including test procedures required to obtain said test data and requirements for the managing of said stored data by only certain authorized individuals; and means for transmitting said data from said one or more stations to said device, and requiring first confirmation that an individual seeking to manage said stored data is authorized in accordance with said requirements and denying said managing of said stored test data absent said confirmation.

13. A data managing and reporting system according to claim 12 wherein each of said one or more stations is precluded from storing said test data.

14. A data managing and reporting system according to claim 12 wherein said test procedures require the obtaining of said data at said one or more stations by only qualified individuals, and said means further requires second confirmation that an individual seeking to transmit said test data is qualified in accordance with said test procedures, and denies transmission of test data absent said second confirmation.

15. A data managing and reporting system according to claim 14 wherein each of said one or more stations are precluded from storing said test data.

16. A method for managing and reporting test data obtained in laboratories engaged in the development or production of pharmaceutical or chemical products for human use and comprising the steps of:

providing a central depository for storage of said test data;

establishing procedures for receiving said test data at said central depository from one or more remote data-taking stations; said procedures including test procedures required to obtain said test data and requirements for the obtaining of said data by only certain qualified individuals;

transmitting said procedures from said central depository to said one or more stations;

requiring first confirmation that an individual seeking to transmit said data from a given said station is qualified in accordance with said requirements; and denying reception of said test data by said central depository from said given station absent said confirmation.

17. A method according to claim 16 including the step of preventing storage of said data at said one or more stations.

18. A method according to claim 16 wherein said procedures further include requirements for obtaining said data by only certain qualified stations; and including the steps of requiring second confirmation that a station seeking to transmit said data is qualified in accordance with said requirements, and denying reception of said data by said central depository absent said second confirmation.

19. A method according to claim 18 including the step of preventing storage of said data at said one or more stations.

20. A method according to claim 16 including the steps of establishing procedures for managing said test data received and stored at said central depository, and the requirement for managing of said stored test data by only certain authorized individuals; requiring second confirmation that an individual seeking to manage said stored data is authorized in accordance with said requirements; and denying management of said stored data absent said confirmation.

21. A method according to claim 20 including the step of preventing storage of said data at said one or more stations.

22. A method according to claim 20 wherein said procedures further include requirements for obtaining said data by only certain qualified stations; and including the steps of requiring third confirmation that a station seeking to transmit said data is qualified in accordance with said requirements, and denying reception of said data by said central depository absent said third confirmation.

23. A method according to claim 22 including the step of preventing storage of said data at said one or more stations.

* * * * *